(12) United States Patent
Wang et al.

(10) Patent No.: US 6,399,329 B1
(45) Date of Patent: Jun. 4, 2002

(54) PHENOL OXIDIZING ENZYMES

(75) Inventors: Huaming Wang, Fremont; Elizabeth A. Bodie, San Carlos, both of CA (US)

(73) Assignee: Genencor International, Inc., Rochester, NY (US)

( * ) Notice: Subject to any disclaimer, the term of this patent is extended or adjusted under 35 U.S.C. 154(b) by 0 days.

(21) Appl. No.: 09/468,578

(22) Filed: Dec. 21, 1999

Related U.S. Application Data

(63) Continuation-in-part of application No. 09/338,723, filed on Jun. 23, 1999, which is a continuation of application No. 09/220,871, filed on Dec. 12, 1998, now abandoned.

(51) Int. Cl.$^7$ ............... C12P 21/06; C12N 9/02; C12N 1/20; C07H 21/04
(52) U.S. Cl. ............ 435/69.1; 435/189; 435/252.3; 435/254.11; 435/254.2; 536/23.2
(58) Field of Search ............... 435/189, 69.1, 435/252.3, 254.11; 536/23.2

(56) References Cited

U.S. PATENT DOCUMENTS 6,072,015 A * 6/2000 Bolle et al. ............ 527/400
6,168,936 B1 * 1/2001 Wang et al. ............ 435/189

FOREIGN PATENT DOCUMENTS

| EP | 0 852 260 A1 | 7/1998 |
| WO | WO 99/49020 | 9/1999 |
| WO | WO 00/05349 | 2/2000 |

OTHER PUBLICATIONS

Patent Abstract of Japan, v. 017 (638) (c–1133), Nov. 26, 1993 & JP 05 199881 A (Amano Pharmaceut Co. Ltd).
Koikeda, S. et al., "Molecular cloning of the gene for bilrubin oxidase from *Myrothecium verrucaria* and its expression in yeast," *Journal of Biological Chemistry*, v. 268(25) pp. 18801–18809 1993.
Copy of Search Report.

* cited by examiner

*Primary Examiner*—Nashaat T. Nashed
*Assistant Examiner*—Malgorzata A. Walicka
(74) *Attorney, Agent, or Firm*—Genecor International, Inc

(57) ABSTRACT

The invention relates to phenol oxidizing enzymes encoded by nucleic acids capable of hybridizing to the nucleic acid having the sequence shown in SEQ ID NO: 1 and in particular phenol oxidizing enzymes obtainable from fungus. Particularly provided are nucleic acid sequences and amino acids from *Bipolaris spicifera*, *Curvularia pallescens* and *Amerosporium atrum*, and expression vectors and host cells comprising said nucleic acid sequences encoding phenol oxidizing enzymes. Additionally, methods for producing the phenol oxidizing enzymes as well as methods for constructing expression hosts are disclosed.

26 Claims, 12 Drawing Sheets

| | | | | | |
|---|---|---|---|---|---|
| CTGCCTAGCC | TCACTTGGTA | GCACGCCCTG | TGGCTGGGGG | TCGAAAGGCC | AGTCAATATC | TTGGTCACTG | 80
| CTAATAGTTC | CTTGCTACGC | GCAAAAAGCT | GGGGCACAGA | CTATCAAGTG | AGACATATAG | GATGCATGTC | 160
| TTTCATAGCC | ACAGTTAGG | TGGTGACCTA | CCCGACTTG | CATGCATACG | ACATGCT | TCCATGCAAC | 240
| ATGTATGGGC | ACATGGGGA | TCAGCACC | TCTGCATGCA | GAATAGAACC | CCCTGGTTT | CTTTTCCTTT | 320
| CTCAAGCACG | CGTGAGGGTG | GTTAACTTGA | GCAAGGCGA | GTGGTCTGTT | CACTGGAGGTA | CTCTCTCTTTC | 400
| CCAATCATGA | CCTGCCCCC | CCAGTTTAGCC | CCCATCAGG | CTGTGAAATC | CACTTGGGA | ATCCTAGCCT | AGTGCTACTC | 480
| TTCAATAGTT | GCTCCTGATG | GGGCACTTTG | GTCACATGC | CTTGGTTTCT | TCTCTTCCGC | ATCAAGCCTC | 560
| TATGCCCGAC | GACACACCT | CATTGGCGG | GACCACTTTG | AGGGGCACG | CACCTTCGG | CGAAGGAGT | TGATAACAC | 640
| CTTCACCCTT | GCCAATGAT | GGAGTTTTGG | TCTATTTGTC | ATGATCAACT | CACATCAACGA | TCCTGAAGA | 720
| GGGTGTGGAA | GCACAACAG | CTTGTCCCTG | TTCTTGCAGA | CTCAGGTCAG | CTCCTAGCGG | CTATACACACG | 800
| CAAGTCCCGT | AAAGTCACA | CCCTTTTCAT | TGCCTAATTT | GCCTATCTC | TATGCGGTTCT | TCAGGATTAT | CAGCGGTCTT | 880
| GCCTACACTC | CCTGCCATG | CGTGAGCAT | ATAAAAGGTCT | CCGAATCCTC | GGTGAAGTCA | ACTCTTCCT | GAATGTCTC | 960
| TCCACACCAG | TCAACACAA | GCTTCTTTCT | CTTACAGCTT | AGCCTGAGCA | CATTCAGACA | ACTCTTCCT | TCTTTTGTC | 1040
| AATATCTGT | TCAAGTCATG | GCAACTGGCA | GCAGCCTCG | GCTCCTGTC | TGGAGTCCTC | GGATCCGTC | TGACACCGG | 1120
| CAGCCACCC | ATTGAGGGTG | TGACTCGA | AGTGAAGACT | GAGGCTTG | CTGACTCCT | CTGACTCCTCA | GCAGGGATG | 1200
| AGGACTGGGA | GTCACTCCA | TACAACTGC | TTTACAGGTG | AGACACGGTG | CCCACCTGT | TTCCCTCGAT | AACTAACTCT | 1280
| TATAGGAATG | CCCTCCCAAT | TCCAACTA | AACGACCA | AGATGATGT | CTTTGATTT | CTAGCAAGCA | ACTCGCCC | 1360
| GACTAATGTA | TTCTAGGATC | ATTACCAAC | CTGTCACCGG | CAAGGACATT | TGTACTATG | AGATGGAGAT | CAAGGCCATT | 1440
| CAGCAAAGG | TGAGTTTGCT | CAGAAACCTT | GTGTAATTA | CTGACCCTTT | CAGACCTTCA | CTGACCTTAC | CCACTTCCG | 1520
| CCCTGCCACT | CTGCTGCCGT | AGCGGCAT | GAGCCCTTC | CCTACTTTCA | ATGTTCCCAG | AGGAACAGAG | ACTGTAGTTA | 1600
| GGTTCATCAA | CAATGCCCTC | CGGTCCATCT | GCACCCTC | CATGCGGTG | CCATGGTTG | CCCTTTTGA | TGGTTGGCT | 1680
| GAAGATGTGA | CCTTGCCTGG | CGAGTACACAG | GATTATCACT | TCCCAACTA | CGCCTTCTGT | GGTACCATGA | 1760
| CCAGCTTTTC | ATGAAGGTAT | GCTTACGAGCC | TTTATCTTTC | TTGGCTACCT | AACTTCCTTT | CGTAGACTGC | 1840
| TGAGAATGCA | TACTTTGTC | AGCCTGGGCC | CTACACATATC | AACGACGAGG | CTGAGGATGC | TCTCGGTCTT | CCTAGTGGCT | 1920

FIG._1A

| | | | | | |
|---|---|---|---|---|---|
| ATGGCGAGTT | CGATATCCT | CTGATCCTGA | CGGCCAAGTA | CTATAACCCC | GATGGTACCC | TGGTTTGAC | CGAGGGTGAG | 2000 |
| GACCAGGACC | TGTGGGAGA | TGTCATCCAT | GTCAACGGAC | GTCCTTGCCT | AGCCATGGCC | TTTCCTTAAC | GTCAGACCG | 2080 |
| TTTCGATTC | CTCAAGCTG | CCGTGTCG | TGCTTGGCTC | CTCTACCTG | TCAGGACCAG | CCTCTCCAAC | GTCAGAATTC | 2160 |
| CTTCCAAGT | CATTGCCTCT | GATGCTGTC | TCTTCAAGC | ACCTCTTGCT | ACCTCTACCTTG | TCTACCTTGC | TGTTGCGAG | 2240 |
| CGTTAGGAGA | TCATTATTGG | TATGCCCTC | CCCTTCAGA | ATGAGTCAAG | AACTCTAAGA | CTAACACTTG | TAGACTTCAC | 2320 |
| CAACTTTGCT | GGCCAGACTC | TTGACTTGG | CAAGGTTGCT | GAGACCAAG | ATGTGGGGA | CGAGGATGAG | TACGCTCCA | 2400 |
| CTCTGCAGGT | GATGGCTTTC | GTGGTCAGGT | CTGCCACTGT | CAAGGTTGCT | TGAGGACAAC | AGCCAGTTCC | CCTCCACTCT | CCGTGACGTT | 2480 |
| CCTTTCCCTC | CTCACAAGGA | AGGCCCGGCC | GACAAGCACT | CCTGCCAAG | CCGAGCTCG | GCACCGTTGA | TGATCAACGA | 2560 |
| TGTTGGCTTT | GCCGATGTCA | ATGAGGGTCT | CCCGAGCTCG | GCACCGTTGA | GGTCGGTGG | CTCGAGAACT | 2640 |
| CCCTCGAGG | CTGGAGCCAC | CCGTTCACA | TTCACTTCGT | TGACTTCAAG | ATCCTCAAGC | GAACTGGTG | TGTGGCCAG | 2720 |
| GTCATGCCT | ACGAGTCTGC | CCGGTCTTAAG | GATGTCGTCACA | GGGTCGCA | CTGACCATG | AGGCCACTA | 2800 |
| CCAACCCTG | ACTGACAGCTT | ACATGTGGA | CTGTCACAAC | CTCATTCAAG | AGGATAACGA | CATGATGCT | GTATTCAACG | 2880 |
| TCACGCCAT | GGAGAGAAG | GGATATCTTC | CGAGACCC | ATGAACCCA | CACTGCCCGA | AGTGCCGGC | CGTTCCTTAC | 2960 |
| AACGCAACG | ACTTCCTGG | TCGGCGTGG | AACTTCTCG | CCGAGTCCAT | CGGCAGGAC | GTGCAGAGCA | TGGCCGAGCA | 3040 |
| GGAGCGTAC | AACGGCCTG | ATGAGACTG | ATGAGATCTT | CGGAGATCT | AGTAAACCCC | GAGCCACAAG | CTCTACAATC | 3120 |
| GTTTTGAGTC | TTAAGACGAC | GCTCTTGTG | CGTATCTTT | CGTATTCTT | TCTTCCCTAC | GGGAACTCC | CTTACACTTG | GGATGTGAA | 3200 |
| GGACATCAAA | AAAGCAAGT | ATATATATTGA | CTCACCACTG | TCATTACCGC | COACTTGTATT | COACTTGATT | CTTGTTCAAA | 3280 |
| CTTTTTCTAGT | COGAGAGTGT | CCATAGTCAA | GAAAGCCCA | TAGGCTATC | GTCTAAACTG | AACTATTGTG | TGTCTGTGA | 3360 |
| CGTGGAGTAG | ATGTCAATTG | TGATGAGACA | CAGTAAATAC | GGTATATCTT | TTCCTAGGAC | TACAGGATCA | GTTTCTCATG | 3440 |
| AGATTACATC | CGTCTAATGT | TGTCCATGA | GAGTTCACT | AAGGTTAGA | ATGCATAGCT | TCCTAGGAC | TGATGCTCTC | 3520 |
| AGCTGTATT | ACGATGTAA | GACAAGTTAG | GTAAGTTTGA | TGTATCGGA | AAATGACTCA | GGCTCCCTA | TTAAGTTGCA | 3600 |
| TGTGAAAACC | TTCAGCAACT | CATGGGTGTT | GGGACCAAAT | CATCCATAAC | TGATTTTGAT | AACTGACCTG | GGTCAAT | 3677 |

FIG._1B

```
GTGGCGTCGG GGATCCACCT GAATCATGAG ATATAAAGAG AGGGATGTTC TGTCAACAAT AATCCCATCA TCAGCTTTTG    80
AACATTCTCA GCTCATCAAA GCTCATCAAA GATTTTCTTC AAGATGGTCG CCAAATACCT CTTCTCAGCA CTTCAACTCG TTTCAATTGC   160
GAAAGGCATA TACGGYGTCG CTTTGAGCGA ACGTCCCGCC AAATTTGTCG ACAACACCCC CGACGAAGAA AAGGCTGCCT   240
TGGCGTCAAT TGTTGAAGAT GACCCTGCGG ATGTTGTCAA CATGCTGAAA GACTGGCAAA GCCCGAGTA TCCTCTCATT   320
TTTCGCCAAC CACTGCCCAT CCCTCCAGCC AAGGAACCAA AGTAGTGAGT GTTCAATCGC ATCGACAGGT TTCTTAGAAT   400
ATACTCACCA TCCACAGTAA ACTCACGAAT CCTGTCACAA ACAAGGAGAT ATGGTACTAC GAGATTGTCA TCAAACCCTT   480
CACCCAGCAG GTCTATCCAA GCCTGCGCCC TGCTCGTTTA GTAGGCTATG ACGGCATCTC CCCAGTTCCT ACGATCATAG   560
TGCCGAGAGG AACAGAAGCT GTTGTACGGT TTATAAACCA GGGTGATCGC GAAAGCTCCA TCCATCTCCA CGGCTCCCCC   640
TCCCGTGCCC CTTTTGACGG ATGGGCTGAT GATATGATCA TGAAGGGGA ATACAAAGGT ACGATAGCGT GTGATTCTAC   720
GCATCAAGAA GCCTCTATCA TACTAACAGG ACTTTCTTCT CAGACTACTA AACCAAGCTG CCAGATTTTT   800
GTGTACCAC GATCATGCTA TGCATGTTGT AAGTCTTTAC CGACTTTTCA TGGTAGTGAA ACGAAGGAT TAAGCTAACA   880
TCTGTGCAGA CCGCAGAAAA TGCCTATTTC GGGCAAGCCG CGCCCTACCT GATCACAGAC CCGGCTGAGG ATGCTCTCGG   960
CCTTCCTTCA GGTTACGGAA AATACGACAT TCCGCTGGTC CTCAGTTCCA AGTACTACAA CGCCGATGGA ACTCTTAAGA  1040
CCAGTGTGGG AGAAGACAAG AGTGTTTGGG GCGACATCAT CCATGTCAAC GGTCAGCCCT GCCATTCTT AAATGTTGAG  1120
CCTCGAAAGT ATCGTCTTCG ATTCCTCAAC GCGGCTGTTT CTAGGAACTT TGCCCCTTAC TTCGTCAAGC AAGACAACAC  1200
TGCCACTAGG CTTCCTTTCC AGTCATTGC CTCTGATGCA GGGCTACTCA CACACCCGGT TCAAACCTCA GATATGTATG  1280
TTGCAGCCGC AGAACGCTAC GAGATTGTGT TCGATTTCGC GCCCTATGCC GGCCAAACGT TGGATCTGCG CAACTTCGCA  1360
AAGGCCAATG GTATCGGTAC CGACGACGAC TACGCAAACA CTGACAAGGT CACGTCAGCA GCCAAAACAGT CATCACTTCC  1440
CGTCGATAAC TCCGTGTAC CCGACGCAGT ATCTCAGATC CAGTTCCCCG CGGGTTTGCA GACGTGTTCT TGCCAAGGTA  1520
GTTTCCATCG TACCAACGGC GAGTGGCGCA TCAACGGCAT CCGGCGGCTG GTCACACCCC ATCCACGTCC ACCTAGTAGA  1600
CCGCGCGGTA CTGTCGAGCT TTGGGAACTT GAGAACAGCT CGGCGACGA AGGCACTCGC CCTATGAGGC CGCCGGTCTC AAGGACGTCG  1680
CTTCCGAGTC GTCGCACGCT ACGGCGACGA AGGCGACACA TTACGCCCCA TGGGACGGAG TCTACATGTT CCACTGCCAC  1760
TGTGGCTCGG CCGTCACGAG AGACATGATG TCGAAGCACA GCCGCCTTCG ACGTGACTAA ACTCCAGAAC TTTGGGTACA ACGAGACGAC  1840
AACCTCATCC ACGAAGACCA AGACATGATG ATCCTCGCTG GTCAGCAAGA CCTTTCACCG CGGGTGATCT CACGGCGCGA TCGGGTATCT  1920
TGATTTCCAC GATCCTGAGG ATCCATCAGG GCTAGAGTAA ATGAGTTGGC GCTCGAGCAG CCTTACACG AACTCGCACA AGTTACAGCC  2000
TTTCAGAAGA ATCCATCAGG GCTAGAGTAA ATGAGTTGGC AAACGCCACG ACGAGTGCGA ACGAGTGCCT GCTGCCCTA TCCCCCGTTA  2160
TCGCTCGAGC AGTACTACAA GACGAACCAG GCTAGAGTAA AAACGCCACG ACGAGTGCGA AGACATGCCT GCTGGCCCTA TCCCCCGTTA  2160
TCGTAGGTTT CAGGTCTGAT TCAAGTTGTT TTGGTGGTGC AACTTCTCCT TCTTCTCTCC ATTGAACTTA ATTGTAGATG  2240
ATGGATACAC ACTCACTTCT CCCTTTCTAT CTCGACGCTT TGGCCATTTT ATTTGTCTT ATTGTGCTAT ATACTGTCTA  2320
TTTCTCTTTC GTATACGAGC AATGTATGTC TTGGTCGGAG TCTGTGGAGT CTGCTGAGGT GACACCTCGC GACGCCATCT  2400
TAGCAGTTTT CGTAACTCTC GTCTATTTGT GATTACTTTG TTCCTTAATC AGTAACAGCT TGAATGTTAGA TTAGCAATGA  2480
GACGAACGAT GAAGCAATCT GAGATGGATC CTTTTTTTT CCTAATATTT GTATACTAAA GAATGTAACAC AATGCCGTTT  2560
TATGAAATGC TCATAACATG CAGCATATTT ACTTTGTTCT ATTTCATTTC ATTTTCATAT GTACGCATAT CCTCGGCATC  2640
AGACAAGAGA CGCGACAACG CTCTCTGCAT CCCTTCTCGG CCGTAATTC CCGTAATATC GCGGATGCGC AAAGCAGTCC  2720
TCCACGCGCT CCATGCTCAT CATGCTCGCT CTATGTATC ACTATGTATC GCGGATGCGC CGGATGTCGC TGCGAACCCA  2800
TTGAATGGGC ATCACGACAG CCATCATGTC CCATCATGTC GATTCTTCTT GCTAAGGACG GCGATGCAAT GCTTGTGAGG GGGTTTTCTG  2880
CATCCCCAGCA AGATGAGGTG GATCC
```

FIG._2

```
MVAKYLFSAL QLVSIAKGIY GVALSERPAK FVDNTPDEEK AALASIVEDD  50
PADVVNMLKD WQSPEYPLIF RQPLPIPPAK EPNKLTNPVT NKEIWYYEIV 100
IKPFTQQVYP SLRPARLVGY DGISPGPTII VPRGTEAVVR FINQGDRESS 150
IHLHGSPSRA PFDGWADDMI MKGEYKDYYY PNNQAARFLW YHDHAMHVTA 200
ENAYFGQAGA YLITDPAEDA LGLPSGYGKY DIPLVLSSKY YNADGTLKTS 250
VGEDKSVWGD IIHVNGQPWP FLNVEPRKYR LRFLNAAVSR NFALYFVKQD 300
NTATRLPFQV IASDAGLLTH PVQTSDMYVA AAERYEIVFD FAPYAGQTLD 350
LRNFAKANGI GTDDDYANTD KVMRFHVSSQ TVVDNSVVPE QLSQIQFPAD 400
KTDIDHHFRF HRTNGEWRIN GIGFADVENR VLAKVPRGTV ELWELENSSG 450
GWSHPIHVHL VDFRVVARYG DEGTRGVMPY EAAGLKDVVW LGRHETVLVE 500
AHYAPWDGVY MFHCHNLIHE DQDMMAAFDV TKLQNFGYNE TTDFHDPEDP 550
RWSARPFTAG DLTARSGIFS EESIRARVNE LALEQPYSEL AQVTASLEQY 600
YKTNQKRHDE CEDMPAGPIP RYRRFQV
```

FIG. 3

```
M-----LFKSWQLAAASGLLSGVLGIPMDTGSHPIEAVDPEVKTEVFADSLLAAAGD------DDWESPPYNLLYRNALPIPPVKQPKMIITNPVTG    86
  :    ::::::::::: ::::::: :  :   ::   ::::   ::  :::::: : :::::::                                 91
MVAKYLFSALQLVSIA---KGIYGVALSERPAKFVDNTPDEEKAALASIVEDDPADVVNMLKDWQSPEYPLIFRQPLPIPPAKEPNKL-TNPVTN

KDIWYYEIEIKPFQQRIYPTLRPATLVGYDGMSPGPTFNVPRGTETVVRFINNATVENSVHLHGSPSRAPFDGWAEDVTFPGEYKDYYFPNYQSA   180
 : :::::: :::: :  :::::::  :::::: :::  ::::::: ::: :: :::::::::::::::::  :::::::::: :::::       186
KEIWYYEIVIKPFTQQVYPSLRPARLVGYDGISPGPTIIVPRGTEAVVRFINQGDRESSIHLHGSPSRAPFDGWADDMIMKGEYKDYYPNNQAA

RLLWYHDHAFMKTAENAYFGQAGAYIINDEAEDALGLPSGYGEFDIPLILTAKYYNADGTLRSTEGEDQDLWGDVIHVNGQPWPFLNVQPRKYRF   276
: ::::::::: : ::::::::::::: :::::::::::::: :: :::: ::::::::  :: :: ::   :::::::::::::::::::::   281
RFLWYHDHAMHVTAENAYFGQAGAYLITDPAEDALGLPSGYGKYDIPLVLSSKYYNADGTLKTSVGEDKSVWGDIIHVNGQPWPFLNVEPRKYRL

RFLNAAVSRAWLLYLVRTSSPNVRIPFQVIASDAGLLQAPVQTSNLYLAVAERYEIIIDFTNFAGQTLDLRNVAETNDVGDEDEYARTLEVMRFV   371
:::::::::: : ::: :: ::::::::::::::::  :::::::: :::::::::: :: :::::::::::: ::::::::  :::: ::::   376
RFLNAAVSRNFALYFVKQDNTATRLPFQVIASDAGLLTHPVQTSDMYVAAAERYEIVFDFAPYAGQTLDLRNFAKANGIGTDDDYANTDKVMRFH

VSSGTVEDNSQVPSTLRDVPFPPHKEGPADKHFKFERSNGHYLINDVGFADVNERVLAKPELGTVEVWELENSSGGWSHPVHIHLVDFKILKRTG   466
::: :::::::: :  :   ::   :: ::     :::   ::::::::::::::::::::::::::::::::::::::: :::::: : :::   470
VSSQTVVDNSVVPEQLSQIQFPADKTD-IDHHFRFHRTNGEWRINGIGFADVENRVLAKVPRGTVELWELENSSGGWSHPIHVHLVDFRVVARYG

GRGQ---VMPYESAGLKDVVWLGRGETLTIEAHYQPWTGAYMWHCHNLIHEDNDMAVFNVTAMEEKGYLQE-DFEDPMNPKWRAVPYNRNDFHAR   558
 :     :::::: ::::::::::: :: ::::: :::: ::: :::::::::::::: :::::: :   :: ::  : : :  :: ::: ::   565
DEGTRGVMPYEAAGLKDVVWLGRHETVLVEAHYAPWDGVYMFHCHNLIHEDQDMMAAFDVTKLQNFGYNETTDFHDPEDPRWSARPFTAGDLTAR

AGNFSAESITARVQELAEQEPYNRLDEILEDLGIEE                                                              594
 :  ::::: :: ::   ::::  :::                                                                       627
SGIFSEESIRARVNELALEQPYSELAQVTASLEQYYKTNQKRHDECEDMPAGPIPRYRRFQV
```

FIG._4

```
GTCAATATGCTGTTCAAGTCATGGCAACTGGCAGCTGCGGCCTCCGGCCTCCTGTCTGGAGTCCTGGGCATCCCGATGGACACGGGCAGCCAC          90
            M  L  F  K  S  W  Q  L  A  A  A  A  S  G  L  L  S  G  V  L  G  I  P  M  D  T  G  S  H    28

CCCATTGAGGCTGTTGATCCGGAAGTGAAGACTGAGGTCTTCGCTGACTCCCTCGCAGCGGCGATGGACGATGATTGGGAGTCCCT                180
  P  I  E  A  V  D  P  E  V  K  T  E  V  F  A  D  S  L  A  A  A  G  D  D  D  W  E  S  P               58

CCCATACAACTTGCTTTACAGGAATGCTTTACCGCCAATTCACCTCCAGTCAAGCAGCCCAAGATGATCATTACCAACCCTGTCACGGCAAGGAC          270
  P  Y  N  L  L  Y  R  N  A  L  P  I  P  P  V  K  Q  P  K  M  I  I  T  N  P  V  T  G  K  D           88

ATTTGGTACTATGAGATCAAGCCATTTCAGCAAAGATTACCCACCTTGCGCCTGCCACTCTGGTGGGCTACGATGGCATG                       360
  I  W  Y  Y  E  I  K  P  F  Q  Q  R  I  Y  P  T  L  R  P  A  T  L  V  G  Y  D  G  M              118

AGCCCTGGTCCTACTTTCAATGTTCCAGAGGACTGAGTTCATCAACAATGCACGTGAGAACTCGTCATCTG                               450
  S  P  G  P  T  F  N  V  P  R  G  T  E  T  V  V  R  F  I  N  N  A  T  V  E  N  S  V  H  L         148

CACGGCTCCCATGCGTCCCCTTTCGATGGTTGGCCTGAAGATGTTACCTTCCCTGGAGAATACAAGGATTACTACTTCCCAACTAC                540
  H  G  S  P  S  R  A  P  F  D  G  W  A  E  D  V  T  F  P  G  E  Y  K  D  Y  Y  F  P  N  Y        178

CAATCGGCCCGCTTCTGTGTACCATGACCATGCCTTCATGAAGACTGCAGAAATGCTACTTTGTCAGGCTGCCCTACATTATC                    630
  Q  S  A  R  L  L  W  Y  H  D  H  A  F  M  K  T  A  E  N  A  Y  F  G  Q  A  G  A  Y  I  I      208

AACGACGAGGCTGAAGATGCTCTCGGTCTTCCTAGTGGCTATGGAGAGTTTGATATCCCTGATCCTGATAATGCC                            720
  N  D  E  A  E  D  A  L  G  L  P  S  G  Y  G  E  F  D  I  P  L  I  L  T  A  K  Y  Y  N  A      238

GATGTACCTCGTTCACCGAGGTGACCAGGACCTGTGGGGAGATGTCATCATGTCAACGACACCATGGCCTTTCTTAAC                         810
  D  G  T  L  R  S  T  E  G  E  D  Q  D  L  W  G  D  V  I  H  V  N  G  Q  P  W  P  F  L  N     268

GTCCAGCCCCGAAGTACGTTTCGATTCCCGCGTCTGCTTCCTCTACCTGTCAGGACCAGCTCCCAAC                                    900
  V  Q  P  R  K  Y  R  F  R  F  L  N  A  A  V  S  R  A  W  L  L  Y  L  V  R  T  S  S  P  N     298
```

*FIG._5A*

```
GTCAGAATTCTTCCAAGTCATTGCCTCGATGCTGGTCTCCTTCAAGACCCTGTTCAGACCTCTACTTGTGTGGGAG    990
  V  R  I  P  F  Q  V  I  A  S  D  A  G  L  L  Q  A  P  V  Q  T  S  N  L  Y  L  A  V  A  E    328

CGTTAGAGATCATTATTGACTTCACCAACTTTGCTGGCCAGACTTTGGACCTGAGAAATGTTGCTGAGACAAATGATGTGGGTGAGAG   1080
  R  Y  E  I  I  I  D  F  T  N  F  A  G  Q  T  L  D  L  R  N  V  A  E  T  N  D  V  G  D  E    358

GATGAGTACGCTCGCACTCTGGAGGTGATGCGTTTCGTTGTGTCAAGTGGTGTCGAGGACAACAGCCAGGTCCCTTCACTCTCGT   1170
  D  E  Y  A  R  T  L  E  V  M  R  F  V  V  S  S  G  T  V  E  D  N  S  Q  V  P  S  T  L  R    388

GAGGTTCCTCCCTCACAAGGAAGGCCCCGCAGACAAGCACTTCAAGTTTGAACGCAGCAACGGACACTACTTGATCAACGATGTT   1260
  D  V  P  F  P  P  H  K  E  G  P  A  D  K  H  F  K  F  E  R  S  N  G  H  Y  L  I  N  D  V    418

GGCTTTGCCGATGTCAATGAGCGGGTGCTGGCCAAGCCGGAGCTGGGAACTGTTGAGGTCGAGTGGGAGCTCGAGAACTCTCTGAGCTGG   1350
  G  F  A  D  V  N  E  R  V  L  A  K  P  E  L  G  T  V  E  V  E  W  E  L  E  N  S  G  G  W    448

AGCCACCCCGTCCATATTCACTTGTTGACTTCAAGATCCTTAAGAGGACCGGAGGTCGTGGCCAGGTCATGCCCTACGAGTCTGCTGGT   1440
  S  H  P  V  H  I  H  L  V  D  F  K  I  L  K  R  T  G  G  R  G  Q  V  M  P  Y  E  S  A  G    478

CTTAAGGATGTGGTCTGGTTGGGCAGGGGTGAGACCCTGACCATTGAGGCCCATTACCAACCTGGACTTACATGTGCACTGT   1530
  L  K  D  V  V  W  L  G  R  G  E  T  L  T  I  E  A  H  Y  Q  P  W  T  G  A  Y  M  W  H  C    508

CACAACTTCATTCACGAGGATAACGACATGATGGCTGTATTCAACGTGACCGCCATGGAGGAGAAGGGATATCTTCAGGAGACTTCGAG   1620
  H  N  L  I  H  E  D  N  D  M  M  A  V  F  N  V  T  A  M  E  E  K  G  Y  L  Q  E  D  F  E    538

GACCCCATGAACCCAAAGTGGCGGGCCGTTCCTTACAACCGTAACGACTTCCATGCTCGCGGCGAAACTTCTCCCGAGTCCATCACT   1710
  D  P  M  N  P  K  W  R  A  V  P  Y  N  R  N  D  F  H  A  R  A  G  N  F  S  A  E  S  I  T    568

GCCCGAGTGCAGGAGCTGGCCGAGCAGGAGCCGTACAACCGCCTGGATGAGATCCTCGAGGATCTTGGAATTGAGGAGTAA   1791
  A  R  V  Q  E  L  A  E  Q  E  P  Y  N  R  L  D  E  I  L  E  D  L  G  I  E  E                594
```

*FIG._5B*

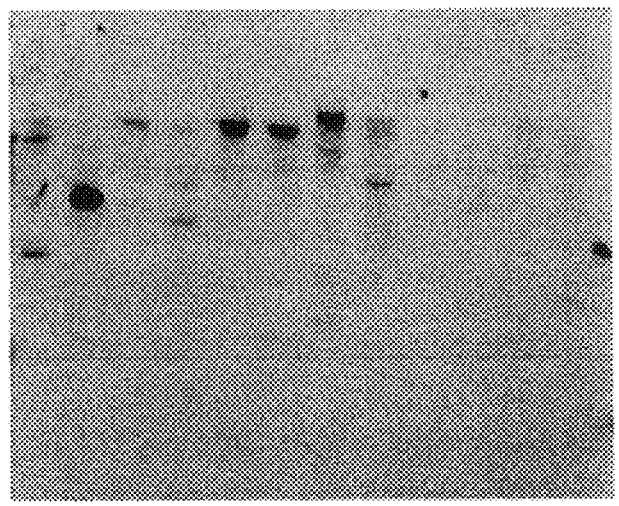
FIG._6
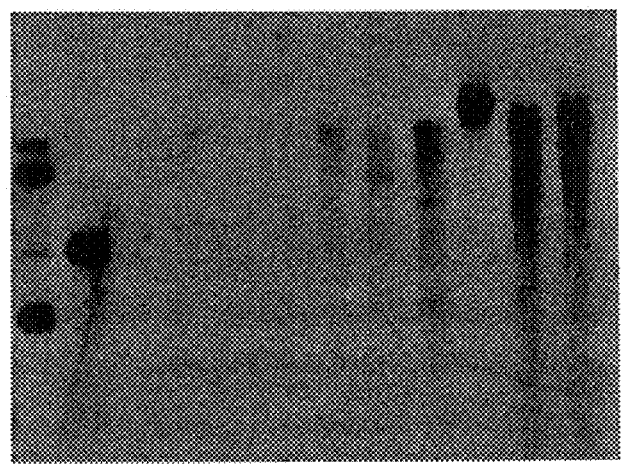
FIG._7
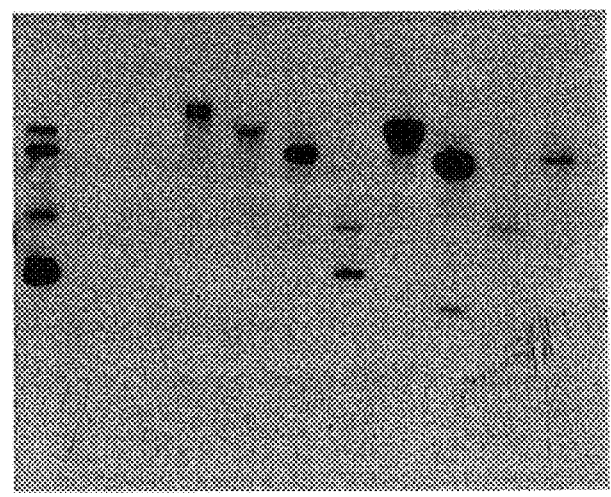
FIG._8

```
ATGGTTGCCA AATACCTCTT CTCGGCACTT CAACTGCCTT CAATTGCGAA AGGCATATAC GGCGTTGCTT TGAGCGAGCG TCCTGCCAAA TATATTGACG  100
AAACCCCCGA CGAAGAAAAG GCTGCCCTGG CAGCCATCGT TGAAGATGAC CCTGCCGATG TTTTCAGAAT CCTGAAGGAC TGGCAAAGCC CGGAGTATCC  200
CATCCTTTTT CGCGAGGCAC TGCCCATCCC TCCAGCCAAG AACCGAAGT AGTGAGTCTT GAATTGCATG GACAGGTTTC CTAGAATATG CTCACCCATC  300
CGCAGTAAAA TGACGAATCC TGTCACAAAC AAGGAGATCT GGTACTACGA GATTGTCATC AAACCCCTTA ACCAACAGGT CTATCCAAGT CTACGTCCTG  400
CTCGCTTGGT AGGCTATGAT GGCATTTCAC CAGGCCCTAC CATCATCGTG CCGAGAGGAA CAGAAGCCGT TGTACGATTC GTAAACCAGG GTGATCGCGA  500
GAGTTCGATT CATCTTCATG GTTCTCCCTC CGGTGCCCCC TTTGACGGAT GGGCTGAAGA TTTGATTATG AAGGCCAAT TCAAAGGTAC AACAGAACAA  600
TCTTATGCAT CAGGGTGCCT CTTTTATACT AACACGACTC GTTCTTAGAC TACTACTACC CGAACAACCA GGCTGCCAGA TTCCTGTGGT ACCACGATCA  700
TGCTATGCAT GTTGTAAGTC TTGCAGAGTA ATCATGGGAG CGAAACGGAA AGATCGGGCT CAGACTGCGG AAAATGCCTA TTTTGGACAG  800
GCTGGCGCCT ACCTGATCAC AGACCCAGCT GAGGACGCCC TCGGCCTTCC TTCGGGTTAC ACATCCCACT GGTGCTCAGT TCCAAGTTCT  900
ACAACAGTGA TGGAACTCTC CAGACCAGTG TGGGAGAAGA CAACAGTTCT CATCCATGT CAACGTGCAG CCCTGCCCAT TCTTCAACGT 1000
TGAGCCTCGA AAGTATCGCC TTCGATTCCT CAATGCGGCT GTTTCTCCGA ACTTTGCCCT CAGAGATATT TACGTGGCAG CCACTGCTAC TAGACTTCCT 1100
TTCCAGGTCA TTGCCTCTGA TGTAGGGCTA CTCACGCACC CGGTCCAAAC TGCAAAGGCC AATGGGGTCG GCACGATGA CGATTATGCA GTATTCGACT 1200
TTGCGCCTTA TGCAGGCCAG ACGATAGATT CAGTCGTCGA TAACTCGGTG GTACCCGCAC AGCTATCTCA CCCGCCGACA AACACCGGCAT CGACCACCAC 1300
CTTCCATGTC AGCAGCCAAG ATCGCCACCA CAGCGAGTGG TGCATCAACG GCATCGGGTT TGCAGACGTC CAGAACCGTA TCCTGGCCAA GGTACCGCGC GGCACTGTCG 1400
TTCCGCTTCC ATCCGGAGAA ACTCGAGAAC AGTCCGGCG ATCCCCTACG AGTCCGCCGG TCTCAAGGAC AGTCCTGGCC GTCGTCAGA CGAGACGGTG CTCGTCAGAC ACGAAAGCAC 1600
TCGCGGCGTC ATGCCGCGTC AGTCCCTACG ATCCACGGA TCCAACCTG CCACAACCTG ATCCACGAAG GATGGCCGCG TTTGACGTGA CTAAGCTCCA CACACTACGC CCCTGGGAC 1700
GGAGTCTACA TGTTCCACTG CCACAACCTG ATCCACGAAG ACCAGACAT ACCAAGACAT AAGACCCTTC GCTGGTCTGC GCGATCGGGT ACTTGACGGC TACAACGAGA 1800
CGACGGATTT CCACGACCCG GAAGATTCTC GCTGGTCTGC ACAGCCGTAC TGGCGCTGGA GCGAACTGG ACAGCCGTAC AGCCGCGGCTG ACGCGGCTG CACAGGTCAC AAGCATCCAT 1900
CAGGGCTAGA GTGAACAGAT GCGCGTGGA ACAGCCGTAC TGGCGCTGGA ACAGCCGTAC TGGCGCTGGA GCGAACTGG ACAGCCGTAC CACAGGTCAC GAGCAGTACT CAAGAAACGC 2000
CAGGCCGAGT GCGAAGACAT GCCTGCTGGC CCCATTCCCC GTTATCGCAG GTTTCAGGTC TGA                                                      2063
```

FIG._9

```
MVAKYLFSAL QLASIAKGIY GVALSERPAK YIDETPDEEK AALAAIVEDD PADVFRILKD WQSPEYPILF REALPIPPAK EPNKMTNPVT NKEIWYEIV  100
IKPFNQQVYP SLRPARLVGY DGISPGPTII VPRGTEAVVR FVNQGDRESS IHLHGSPSRA PFDGWAEDLI MKGQFKDYYY PNNQAARFLW YHDHAMHVTA  200
ENAYFGQAGA YLITDPAEDA LGLPSGYGKY DIPLVLSSKF YNSDGTLQTS VGEDNSLWGD VIHVNGQPWP FFNVEPRKYR LRFLNAAVSR NFALYFVKQQ  300
ATATRLPFQV IASDAGLLTH PVQTSDIYVA AAERYEIVFD FAPYAGQTID LRNFAKANGV GTDDDYANTD KVMRFHVSSQ AVVDNSVVPA QLSQIQFPAD  400
KTGIDHHFRF HRTNSEWRIN GIGFADVQMR ILAKVPRGTV ELWELENSSG GWSHPIHVHL VDFRVVARYG DESTRGVMPY ESAGLKDVVW LGRHETVLVE  500
AHYAPWDGVY MFHCHNLIHE DQDMMAAFDV TKLQNFGYNE TDDFHDPEDS RWSARPFTAA DLTARSGIFS EASIRARVNE LALEQPYSEL AQVTASLEQY  600
YKTNKKRQAE CEDMPAGPIP RYRRFQV                                                                                         627
```

FIG._10

```
MVAKYLFSALQLASIAKGIYGVALSERPAKYIDETPDEEKAALAAIVEDDPADVFRILKDWQSPEYPILFREALPIPPAK
||||||||||||||||||||||||||||||||| ||||||||||||||||| || ||||||||||||| ||||||||
MVAKYLFSALQLVSIAKGIYGVALSERPAKFVDNTPDEEKAALASIVEDDPADVVNMLKDWQSPEYPLIFRQPLPIPPAK

EPNKMTNPVTNKEIWYYEIVIKPFNQQVYPSLRPARLVGYDGISPGPTIIVPRGTEAVVRFVNQGDRESSIHLHGSPSRA
|||| |||||||||||||||||| ||||||||||||||||||||||||||||||||||||||  |||||||||||||
EPNKLTNPVTNKEIWYYEIVIKPFTQQVYPSLRPARLVGYDGISPGPTIIVPRGTEAVVRFINQGDRESSIHLHGSPSRA

PFDGWAEDLIMKGQFKDYYYPNNQAARFLWYHDHAMHVTAENAYFGQAGAYLITDPAEDALGLPSGYGKYDIPLVLSSKF
||||||  ||||| ||||||||||||||||||||||||||||||||||||||||||||||||||| ||||||||||
PFDGWADDMIMKGEYKDYYYPNNQAARFLWYHDHAMHVTAENAYFGQAGAYLITDPAEDALGLPSGYGKYDIPLVLSSKY

YNSDGTLQTSVGEDNSLWGDVIHVNGQPWPFFNVEPRKYTRLRFLNAAVSRNFALYFVKQQATATRLPFQVIASDAGLLTH
|| |||| |||||| ||||| |||||||| |||||| |||||||||||||||||| | |  |||||||||||||||||
YNADGTLKTSVGEDKSVWGDIIHVNGQPWPFLNVEPRKYRLRFLNAAVSRNFALYFVKQDNTATRLPFQVIASDAGLLTH

PVQTSDIYVAAAERYEIVFDFAPYAGQTIDLRNFAKANGVGTDDDYANTDKVMRFHVSSQAVVDNSVVPAQLSQIQFPAD
||||||| |||||||||||||||||||||||||||||| |||||||||||||||||||| | |||||| ||||||||
PVQTSDMYVAAAERYEIVFDFAPYAGQTLDLRNFAKANGIGTDDDYANTDKVMRFHVSSQTVVDNSVVPEQLSQIQFPAD

KTGIDHHFRFHRTNSEWRINGIGFADVQNRILAKVPRGTVELWELENSSGGWSHPIHVHLVDFRVVARYGDESTRGVMPY
||| |||||||||||| |||||||| || |||||||||||||||||||||||||||||||||||||||||| |||||
KTDIDHHFRFHRTNGEWRINGIGFADVENRVLAKVPRGTVELWELENSSGGWSHPIHVHLVDFRVVARYGDEGTRGVMPY

ESAGLKDVVWLGRHETVLVEAHYAPWDGVYMFHCHNLIHEDQDMMAAFDVTKLQNFGYNETTDFHDPEDSRWSARPFTAA
| |||||||||||||||||||||||||||||||||||||||||||||||||||||||||||||||| ||||||||| 
EAAGLKDVVWLGRHETVLVEAHYAPWDGVYMFHCHNLIHEDQDMMAAFDVTKLQNFGYNETTDFHDPEDPRWSARPFTAG

DLTARSGIFSEASIRARVNELALEQPYSELAQVTASLEQYYKTNKKRQAECEDMPAGPIPRYRRFQV
||||||||||| ||||||||||||||||||||||||||||||||| ||| ||||||||||||||
DLTARSGIFSEESIRARVNELALEQPYSELAQVTASLEQYYKTNQKRHDECECEDMPAGPIPRYRRFQV
```

FIG._11

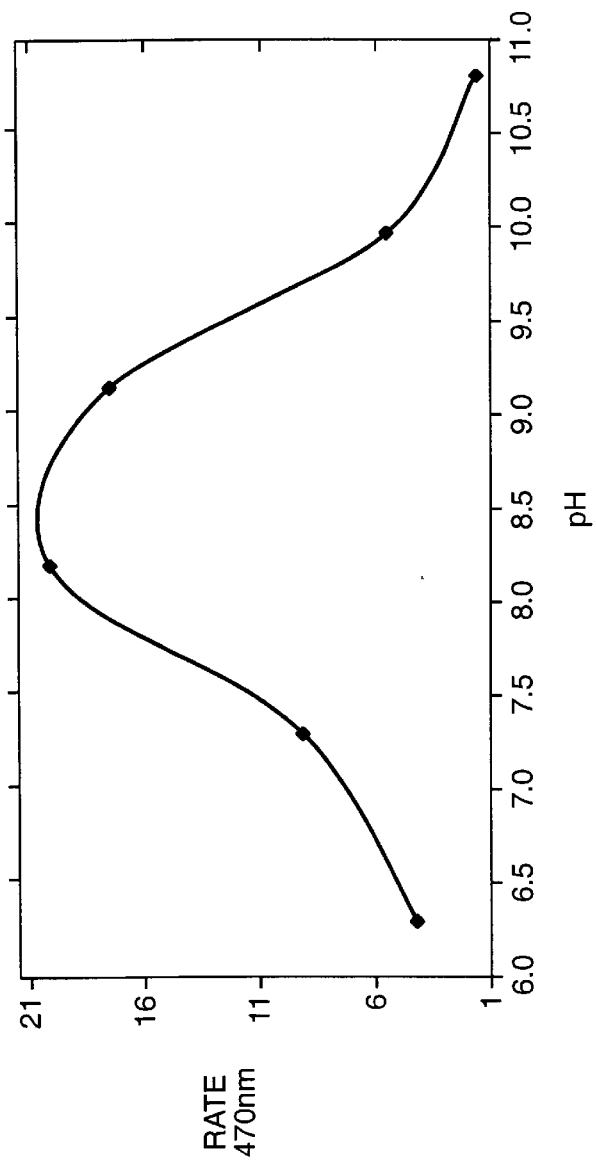

```
CACCGCCGAGAACGCTTACTTTGGTCAAGCTGGCTTTTACATTCTGCACGACCCCGCTGAAGATGCATTGGGTCTG      76
 T  A  E  N  A  Y  F  G  Q  A  G  F  Y  I  L  H  D  P  A  E  D  A  L  G  L
CCTTCTGGCAAGTATGATGTACCTCTTGCACTGTCCTCCAAGCAGTACAACAGCGACGGTACCCTCTTCGACCCCA     152
 P  S  G  K  Y  D  V  P  L  A  L  S  L  K  A  Y  N  S  D  G  T  L  F  D  P
AGGACGAGACCGATTCACTGTTCGGCGATGTCATCCACGTCAACGGACAGCCATGGCCCTACTTTAAGGTCGAGCC     228
 K  D  E  T  D  S  L  F  G  D  V  I  H  V  N  G  Q  P  W  P  Y  L  K  V  E  P
TCGCAAGTACCGTCTCCGCTTCCTCAATGCTGCTATCAGCCGTGCCTTCAAGCTCACTTTCGAGGCTGATGGCAAA     304
 R  K  Y  R  L  R  F  L  N  A  A  I  S  R  A  F  K
GTGATCAACTTTCCTGTCATCGGTGCCGATACTGGTCTCTTGACCAAGCCTGTTCAGACAAGCAACCTTGAGATCT     380
CTATGGCCCGAGCGCTGGGAGGTTGTTTTTGACTTCAGCCAATTTCCGGGAAGAACGTCACCCTCAAGAACGGTCG     456
CGATGTGCAGCACGATGAGGACTACAACTCCACCGACAAAGTCATGCAGTTCGTTGTTGGCAAGGATGTTACGAGC     532
CAGGCTGGTAATGGCAACCTTCCCGGCTCTCTGCGCACTGTTCCCTCCTAAGAAGGGGCGGAGTCGACAGG     608
AGCTTCAAGTTCGGCAGGGACCGGTGGCCAGTGGACTGGAGCTTTGACCTTCGCTGATGTCAACAACCGCATC     684
CTGGCTAAGCCCCCAACGTGGTGCCATCGAGGTTTTGGGAGCTTTGAGAACTTCCAGCGGGNTGGTCTTACCCT     760
                V  W  E  L  E  N  T  S  S  G  G  W  S  Y  P
TGTCCACATCCACCTGGGTCGACTTTCCAGATNCTTGTCTTGCACTGGANGCAAGCNCCCGTTNTAACTNCNAN      836
 V  H  H  L
AAAGGAAGCACTTTCAAGGGCG                                                           858
```

PHENOL OXIDIZING ENZYMES

This application is a continuation in part application of application Ser. No. 09/338,723 filed Jun. 23, 1999, which is a continuation application of application Ser. No. 09/220,871 filed Dec. 12, 1998, now abandoned.

FIELD OF THE INVENTION

The present invention relates to novel phenol oxidizing enzymes, in particular, novel phenol oxidizing enzymes obtainable from fungus. The present invention provides methods and host cells for expressing the phenol oxidizing enzymes as well as methods for producing expression systems comprising the phenol oxidizing enzymes.

BACKGROUND OF THE INVENTION

Phenol oxidizing enzymes function by catalyzing redox reactions, i.e., the transfer of electrons from an electron donor (usually a phenolic compound) to molecular oxygen (which acts as an electron acceptor) which is reduced to H2O. While being capable of using a wide variety of different phenolic compounds as electron donors, phenol oxidizing enzymes are very specific for molecular oxygen as the electron acceptor.

Phenol oxidizing enzymes can be utilized for a wide variety of applications, including the detergent industry, the paper and pulp industry, the textile industry and the food industry. In the detergent industry, phenol oxidizing enzymes have been used for preventing the transfer of dyes in solution from one textile to another during detergent washing, an application commonly referred to as dye transfer inhibition. Most phenol oxidizing enzymes exhibit pH optima in the acidic pH range while being inactive in neutral or alkaline pHs.

Phenol oxidizing enzymes are known to be produced by a wide variety of fungi, including species of the genii Aspergillus, Neurospora, Podospora, Botytis, Pleurotus, Fomes, Phlebia, Trametes, Polyporus, Rhizoctonia and Lentinus. However, there remains a need to identify and isolate phenol oxidizing enzymes, and organisms capable of naturally-producing phenol oxidizing enzymes for use in textile, cleaning and detergent washing methods and compositions.

SUMMARY OF THE INVENTION

The present invention relates to novel phenol oxidizing enzymes encoded by nucleic acid capable of hybridizing to the nucleic acid encoding *Stachybotrys chartarum* phenol oxidizing enzyme (shown in FIG. 1, and having the polynucleotide sequence shown in SEQ ID NO:1), or a fragment thereof, under conditions of high to intermediate stringency, as long as the phenol oxidizing enzyme is capable of modifying the color associated with dyes or colored compounds. In illustrative embodiments disclosed herein, the phenol oxidizing enzymes are obtainable from fungus. The phenol oxidizing enzymes of the present invention can be used, for example, for pulp and paper bleaching, for bleaching the color of stains on fabric and for anti-dye transfer in detergent and textile applications. The phenol oxidizing enzymes of the present invention may be capable of modifying the color in the absence of an enhancer or in the presence of an enhancer.

Accordingly, the present invention provides phenol oxidizing enzymes encoded by nucleic acid capable of hybridizing to the nucleic acid having the sequence as shown in SEQ ID NO:1 or a fragment thereof, under conditions of intermediate to high stringency. Such enzymes will comprise at least 60% identity, at least 65% identity, at least 70% identity, at least 75% identity, at least 80% identity, at least 85% identity, at least 90% identity and at least 95% identity to the *Stachybotrys chartarum* phenol oxidizing enzyme having the amino acid sequence disclosed in SEQ ID NO:2, and specifically excludes the amino acid sequence shown in SEQ ID NO:2, as long as the enzyme is capable of modifying the color associated with dyes or colored compounds. In one embodiment, the phenol oxidizing enzyme is obtainable from bacteria, yeast or non-Stachybotrys species of fungus. In a preferred embodiment, the phenol oxidizing enzyme is obtainable from fungus including Myrothecium species, Curvularia species, Chaetomium species, Bipolaris species, Humicola species, Pleurotus species, Trichoderma species, Mycellophthora species and Amerosporium species. In a preferred embodiment, the fungus include *Myrothecium verrucaria, Curvularia pallescens*, Chaetomium sp, *Bipolaris spicifera, Humicola insolens, Pleurotus abalonus, Trichoderma reesei, Mycellophthora thermophila* and *Amerosporium atrum*.

In an illustrative embodiment disclosed herein, the phenol oxidizing enzyme is obtainable from *Bipolaris spicifera* and has the genomic nucleic acid sequence as shown in FIG. 2 (SEQ ID NO:3) and the deduced amino acid sequence as shown in FIG. 3 (SEQ ID NO:4). In another illustrative embodiment disclosed herein, the phenol oxidizing enzyme is obtainable from *Curvularia pallescens* and has the genomic nucleic acid sequence as shown in FIG. 9 (SEQ ID NO:6) and the deduced amino acid sequence as shown in FIG. 10 (SEQ ID NO:7). In another illustrative embodiment disclosed herein, the phenol oxidizing enzyme is obtainable from *Amerosporium atrum* and comprises the nucleic acid sequence as shown in FIG. 13 (SEQ ID NO: 8) and the deduced amino acid sequence as shown in FIG. 13 (SEQ ID NO:9).

Accordingly, the present invention encompasses phenol oxidizing enzymes encoded by polynucleotide sequences that hybridize under conditions of intermediate to high stringency to the nucleic acid having the sequence as shown in SEQ ID NO:3, SEQ ID NO:6 or SEQ ID NO:8, or a fragment thereof, and which are capable of modifying the color associated with a dye or colored compound. The present invention also encompasses polynucleotides that encode the amino acid sequence as shown in SEQ ID NO:4 as well as polynucleotides that encode the amino acid sequence as shown in SEQ ID NO:7 and polynucleotides that encode the amino acid sequence as shown in SEQ ID NO:9. The present invention provides expression vectors and host cells comprising polynucleotides encoding the phenol oxidizing enzymes of the present invention as well as methods for producing the enzymes.

The present invention provides a method for producing a phenol oxidizing enzyme comprising the steps of obtaining a host cell comprising a polynucleotide capable of hybridizing to SEQ ID NO:1, or a fragment thereof, under conditions of intermediate to high stringency wherein said polynucleotide encodes a phenol oxidizing enzyme capable of modifying the color associated with dyes or colored compounds; growing said host cell under conditions suitable for the production of said phenol oxidizing enzyme; and optionally recovering said phenol oxidizing enzyme produced. In one embodiment, the polynucleotide comprises the sequence as shown in SEQ ID NO:3; in another embodiment, the polynucleotide comprises the sequence as shown in SEQ ID NO:6; and in another embodiment, the polynucleotide comprises the sequence as shown in SEQ ID NO: 8. In another embodiment, the phenol oxidizing enzyme comprises the amino acid sequence as shown in SEQ ID NO:4; in a further embodiment, the phenol oxidizing enzyme comprises the amino acid sequence as shown in SEQ ID NO:7; and in yet another embodiment, the phenol oxidizing enzyme comprises the amino acid sequence as shown in SEQ ID NO:9.

The present invention also provides a method for producing a host cell comprising a polynucleotide encoding a phenol oxidizing enzyme comprising the steps of obtaining a polynucleotide capable of hybridizing to SEQ ID NO:1, or fragment thereof, under conditions of intermediate to high stringency wherein said polynucleotide encodes a phenol oxidizing enzyme capable of modifying the color associated with dyes or colored compounds; introducing said polynucleotide into said host cell; and growing said host cell under conditions suitable for the production of said phenol oxidizing enzyme. In one embodiment, the polynucleotide comprises the sequence as shown in SEQ ID NO:3. In another embodiment, the polynucleotide comprises the sequence as shown in SEQ ID NO:6. In a further embodiment, the polynucleotide comprises the sequence as shown in SEQ ID NO:8. In the present invention, the host cell comprising a polynucleotide encoding a phenol oxidizing enzyme includes filamentous fungus, yeast and bacteria. In one embodiment, the host cell is a filamentous fungus including Aspergillus species, Trichoderma species and Mucor species. In a further embodiment, the filamentous fungus host cell includes Aspergillus niger var. awamori or Trichoderma reesei.

In yet another embodiment of the present invention, the host cell is a yeast which includes Saccharomyces, Pichia, Hansenula, Schizosaccharomyces, Kluyveromyces and Yarrowia species. In an additional embodiment, the Saccharomyces species is Saccharomyces cerevisiae. In yet an additional embodiment, the host cell is a gram positive bacteria, such as a Bacillus species, or a gram negative bacteria, such as an Escherichia species.

Also provided herein are detergent compositions comprising a phenol oxidizing enzyme encoded by nucleic acid capable of hybridizing to the nucleic acid encoding Stachybotrys chartarum phenol oxidizing enzyme (shown in FIG. 1 and having SEQ ID NO:1) under conditions of intermediate to high stringency. Such enzymes will have at least 60% identity, at least 65% identity, at least 70% identity, at least 75% identity, at least 80% identity, at least 85% identity, at least 90% identity and at least 95% identity to the phenol oxidizing enzyme having the amino acid sequence disclosed in SEQ ID NO:2, and will specifically exclude the amino acid having the sequence as shown in SEQ ID NO:2, as long as the enzyme is capable of modifying the color associated with dyes or colored compounds. In one embodiment of the detergent composition, the amino acid comprises the sequence as shown in SEQ ID NO:4. In another embodiment of the detergent composition, the amino acid comprises the sequence as shown in SEQ ID NO:7. In a further embodiment of the detergent composition, the amino acid comprises the sequence as shown in SEQ ID NO:9.

The present invention also encompasses methods for modifying the color associated with dyes or colored compounds which occur in stains in a sample, comprising the steps of contacting the sample with a composition comprising a phenol oxidizing enzyme encoded by nucleic acid capable of hybridizing to the nucleic acid encoding Stachybotrys chartarum phenol oxidizing enzyme (shown in FIG. 1 and having SEQ ID NO:1) under conditions of intermediate to high stringency. Such phenol oxidizing enzymes will have at least 60% identity, at least 65% identity, at least 70% identity, at least 75% identity, at least 80% identity, at least 85% identity, at least 90% identity and at least 95% identity to the phenol oxidizing enzyme having the amino acid sequence disclosed in SEQ ID NO:2, and specifically excludes the amino acid having the sequence as shown in SEQ ID NO:2, as long as the enzyme is capable of modifying the color associated with dyes or colored compounds. In one embodiment of the method, the amino acid comprises the amino acid sequence as shown in SEQ ID NO:4. In another embodiment, the amino acid comprises the amino acid sequence as shown in SEQ ID NO:7. In a further embodiment, the amino acid comprises the amino acid having the sequence as shown in SEQ ID NO:9.

BRIEF DESCRIPTION OF THE DRAWINGS

FIG. 1 provides the genomic nucleic acid sequence (SEQ ID NO:1) encoding a phenol oxidizing enzyme obtainable from Stachybotrys chartarum.

FIG. 2 provides the genomic sequence (SEQ ID NO:3) encoding a phenol oxidizing enzyme obtainable from Bipolarius spicifera.

FIG. 3 provides the deduced amino acid sequence (SEQ ID NO:4) for a phenol oxidizing enzyme obtainable from Bipolarius spicifera.

FIG. 4 is an amino acid alignment of phenol oxidizing enzyme obtainable from Stachybotrys chartarum SEQ ID NO:2 (top line) and Bipolarius spicifera (SEQ ID NO:4).

FIG. 5 is a cDNA (SEQ ID NO:5) and amino acid sequence (SEQ ID NO:2) obtainable from Stachybotrys chartarum.

FIG. 6 is a representation of the Southern hybridization technique described in Example IV. The genomic DNA was isolated from following strains: Stachybotrys chartarum (lanes 1 and 2), Myrothecium verruvaria (lanes 3 and 4), Curvalaria pallescens (lanes 5 and 6), Myrothecium cinctum (lanes 7 and 8), Pleurotus eryngii (lanes 9 and 10), Humicola insulas (lanes 11 and 12). The genomic DNA was digested with restriction enzymes EcoRI (lanes 1, 3, 5, 7, 9, 11) or HindIII (lanes 2, 4, 6, 8, 10 and 12). The DNA probe used for Southern analysis was isolated from a Stachybotrys chartarum genomic fragment generated through PCR that covers the internal part of the genes of more than 1 kb in size. The same DNA probe was used in the Southern hybridization techniques illustrated in FIGS. 7, 8 and 9.

FIG. 7 is a representation of the Southern hybridization technique described in Example IV. The genomic DNA was isolated from following strains: Stachybotrys chartarum (lanes 1 and 2), Aspergillus niger (lanes 3 and 4), Corpinus cineras (lanes 5 and 6), Mycellophthora thermophila (lanes 7 and 8), Pleurotus abalonus (lanes 9 and 10), Trichoderma reesei (lanes 11 and 12). The genomic DNA was digested with restriction enzymes EcoRI (lanes 1, 3, 5, 7, 9, 11) or HindIII (lanes 2, 4, 6, 8, 10 and 12).

FIG. 8 is a representation of the Southern hybridization technique described in Example IV. The genomic DNA was isolated from following strains: Stachybotrys chartarum (lane 1); Trametes vesicolor (lanes 2 and 3); Amerosporium atrum (lanes 6 and 7); Bipolaris spicifera (lanes 8 and 9); Chaetomium sp (lanes 10 and 11). The genomic DNA was digested with restriction enzymes EcoRI (lanes 1, 2, 8 and 10) or HindIII (lanes 3, 9 and 11).

FIG. 9 provides the genomic nucleic acid sequence of a phenol oxidizing enzyme obtainable from Curvularia pallescens from the translation start site to the translation stop site.

FIG. 10 provides the deduced amino acid sequence of the phenol oxidizing enzyme obtainable from *Curvularia pallescens*.

FIG. 11 provides an amino acid alignment between the amino acid sequence obtainable from *Bipolaris spicifera* shown in SEQ ID NO:4 (bottom line) and *Curvularia pallescens* shown in SEQ ID NO:7 (top line).

FIG. 12 shows the *Bipolaris spicifera* pH profile as measured at 470 nm using Guaicol as a substrate.

FIG. 13 shows the *Amerosporium atrum* nucleic acid (SEQ ID NO:8) and deduced amino acid sequence (SEQ ID NO:9).

FIG. 14 provides an amino acid alignment between the amino acid sequence obtainable from *Amerosporium atrum* (SEQ ID NO:9) (bottom line) and the amino acid sequence obtainable from *Stachybotrys chartarum* (SEQ ID NO:2) (top line).

DETAILED DESCRIPTION

Definitions

As used herein, the term "phenol oxidizing enzyme" refers to those enzymes which catalyze redox reactions and are specific for molecular oxygen and/or hydrogen peroxide as the electron acceptor. The phenol oxidizing enzymes described herein are encoded by nucleic acid capable of hybridizing to SEQ ID NO:1 (which encodes a phenol oxidizing enzyme obtainable from *Stachybotrys chartarum* ATCC number 38898), or a fragment thereof, under conditions of intermediate to high stringency and are capable of modifying the color associated with a dye or colored compound. Such phenol oxidizing enzymes will have at least 60% identity, at least 65% identity, at least 70% identity, at least 75% identity, at least 80% identity, at least 85% identity, at least 90% identity and at least 95% identity to the phenol oxidizing enzyme having the amino acid sequence disclosed in SEQ ID NO:2 as determined by MegAlign Program from DNAstar (DNASTAR, Inc. Madison, Wis. 53715) by Jotun Hein Method (1990, Method in Enzymology, 183: 626–645).

As used herein, Stachybotrys refers to any Stachybotrys species which produces a phenol oxidizing enzyme capable of modifying the color associated with dyes or colored compounds. The present invention encompasses derivatives of natural isolates of Stachybotrys, including progeny and mutants, as long as the derivative is able to produce a phenol oxidizing enzyme capable of modifying the color associated with dye or color compounds.

As used herein in referring to phenol oxidizing enzymes, the term "obtainable from" means phenol oxidizing enzymes equivalent to those that originate from or are naturally-produced by the particular microbial strain mentioned. To exemplify, phenol oxidizing enzymes obtainable from Bipolaris refer to those phenol oxidizing enzymes which are naturally-produced by Bipolaris. The present invention encompasses phenol oxidizing enzymes produced recombinantly in host organisms through genetic engineering techniques. For example, a phenol oxidizing enzyme obtainable from Bipolaris can be produced in an Aspergillus species through genetic engineering techniques.

As used herein, the term 'colored compound' refers to a substance that adds color to textiles or to substances which result in the visual appearance of stains. As defined in Dictionary of Fiber and Textile Technology (Hoechst Celanese Corporation (1990) PO Box 32414, Charlotte N.C. 28232), a dye is a colored compound that is incorporated into the fiber by chemical reaction, absorption, or dispersion. Examples of dyes include direct Blue dyes, acid Blue dyes, direct red dyes, reactive Blue and reactive Black dyes. A catalogue of commonly used textile dyes is found in Colour Index, 3rd ed. Vol. 1–8. Examples of substances which result in the visual appearance of stains are polyphenols, carotenoids, anthocyanins, tannins, Maillard reaction products, etc.

As used herein the phrase "modify the color associated with a dye or colored compound" or "modification of the colored compound" means that the dye or compound is changed through oxidation such that either the color appears modified, i.e., the color visually appears to be decreased, lessened, decolored, bleached or removed, or the color is not affected but the compound is modified such that dye redeposition is inhibited. The present invention encompasses the modification of the color by any means including, for example, the complete removal of the colored compound from stain on a sample, such as a fabric, by any means as well as a reduction of the color intensity or a change in the color of the compound. For example, in pulp and paper applications, delignification in the pulp results in higher brightness in paper made from the pulp.

As used herein, the term "mutants and variants", when referring to phenol oxidizing enzymes, refers to phenol oxidizing enzymes obtained by alteration of the naturally occurring amino acid sequence and/or structure thereof, such as by alteration of the nucleic acid sequence of the structural gene and/or by direct substitution and/or alteration of the amino acid sequence and/or structure of the phenol oxidizing enzyme. The term phenol oxidizing enzyme "derivative" as used herein refers to a portion or fragment of the full-length naturally occurring or variant phenol oxidizing enzyme amino acid sequence that retains at least one activity of the naturally occurring phenol oxidizing enzyme.

As used herein, the term "mutants and variants", when referring to microbial strains, refers to cells that are changed from a natural isolate in some form, for example, having altered DNA nucleotide sequence of, for example, the structural gene coding for the phenol oxidizing enzyme; alterations to a natural isolate in order to enhance phenol oxidizing enzyme production; or other changes that effect phenol oxidizing enzyme expression.

The term "enhancer" or "mediator" refers to any compound that is able to modify the color associated with a dye or colored compound in association with a phenol oxidizing enzyme or a compound which increases the oxidative activity of the phenol oxidizing enzyme. The enhancing agent is typically an organic compound.

Phenol Oxidizing Enzymes

The phenol oxidizing enzymes of the present invention function by catalyzing redox reactions, i.e., the transfer of electrons from an electron donor (usually a phenolic compound) to molecular oxygen and/or hydrogen peroxide (which acts as an electron acceptor) which is reduced to water. Examples of such enzymes are laccases (EC 1.10.3.2), bilirubin oxidases (EC 1.3.3.5), phenol oxidases (EC 1.14.18.1), catechol oxidases (EC 1.10.3.1).

The present invention encompasses phenol oxidizing enzymes obtainable from bacteria, yeast or non-Stachybotrys fungal species said enzymes being encoded by nucleic acid capable of hybridizing to the nucleic acid as shown in SEQ ID NO:1 under conditions of intermediate to high stringency, as long as the enzyme is capable of modifying the color associated with a dye or colored compound.

Phenol oxidizing enzymes encoded by nucleic acid capable of hybridizing to SEQ ID NO:1, or a fragment thereof, are obtainable from bacteria, yeast and non-Stachybotrys fungal species including, but not limited to

*Myrothecium verrucaria, Curvalaria pallescens,* Chaetomium sp, *Bipolaris spicifera, Humicola insolens, Pleurotus abalonus, Trichoderma reesei, Mycellophthora thermophila* and *Amerosporium atrum*. Illustrative examples of isolated and characterized phenol oxidizing enzymes encoded by nucleic acid capable of hybridizing to SEQ ID NO:1 are provided herein and include phenol oxidizing enzymes obtainable from strains of *Bipolaris spicifera, Curvularia pallescens,* and *Amerosporium atrum* and include the phenol oxidizing enzymes comprising the amino acid sequences as shown in SEQ ID NO: 4, SEQ ID NO:7, and SEQ ID NO: 9, respectively. The amino acid sequence shown in SEQ ID NO:9 represents a partial amino acid sequence.

Strains of *Bipolaris spicifera* are available from the Centraalbureau Voor Schimmelcultures Baarn (CBS)-Delft (The Netherlands) Institute of the Royal Netherlands Academy of Arts and Sciences and have CBS accession number CBS 197.31; CBS 198.31; CBS 199.31; CBS 211.34; CBS 274.52; CBS 246.62; CBS 314.64; CBS 315.64; CBS 418.67; CBS 364.70 and CBS 586.80.

Strains of *Curvularia pallescens* are available from the American Type Culture Collection (ATCC) and include ATCC accession numbers ATCC 12018; ATCC 22920; ATCC 32910; ATCC 34307; ATCC 38779; ATCC 44765; ATCC 60938; ATCC 60939; and ATCC 60941.

Strains of *Amerosporium atrum* are available from the CBS and include CBS accession numbers, CBS 142.59; CBS 166.65; CBS 151.69; CBS 548.86.

As will be understood by the skilled artisan, there may be slight amino acid variations of the phenol ozidizing enzyme found among the variety of deposited strains of a particular organism. For example, among the variety of *Bipolaris spicifera* strains deposited with the CBS, there may be amino acid sequences having 95% or greater identity to the amino acid sequence shown in SEQ ID NO:4 and similarly, among the variety of *Curvularia pallescens* strains deposited with the ATCC, there may be amino acid sequences having 95% or greater identity to the amino acid sequence shown in SEQ ID NO:7. Additionally, among the variety of *Amerosporium atrum* strains deposited with the CBS, there may be amino acid sequences having 95% or greater identity to the amino acid sequence shown in SEQ ID NO:9. Therefore, the present invention encompasses phenol oxidizing enzymes obtainable from strains of *Bipolaris spicifera* that have at least 95% identity to the amino acid sequence shown in SEQ ID NO:4. The present invention also encompasses phenol oxidizing enzymes obtainable from strains of *Curvularia pallescens* that have at least 95% identity to the amino acid sequence shown in SEQ ID NO:7. The present invention also encompasses phenol oxidizing enzymes obtainable from strains of *Amerosporium atrum* that have at least 95% identity to the amino acid sequence shown in SEQ ID NO:9.

Nucleic Acid Encoding Phenol Oxidizing Enzymes

The present invention encompasses polynucleotides which encode phenol oxidizing enzymes obtainable from bacteria, yeast or non-Stachybotrys fungal species which polynucleotides comprise at least 60% identity, at least 65% identity, at least 70% identity, at least 75% identity, at least 80% identity, at least 85% identity, at least 90% identity and at least 95% identity to the polynucleotide sequence disclosed in SEQ ID NO:1 (as determined by MegAlign Program from DNAstar (DNASTAR, Inc. Maidson, Wis. 53715) by Jotun Hein Method (1990, Method in Enzymology, 183: 626–645) with a gap penalty=11, a gap length penalty=3 and Pairwise Alignment Parameters Ktuple=2) as long as the enzyme encoded by the polynucleotide is capable of modifying the color associated with dyes or colored compounds. In a preferred embodiment, the phenol oxidizing enzyme is encoded by a polynucleotide comprising the sequence as shown in SEQ ID NO:3. In another preferred embodiment, the phenol oxidizing enzyme is encoded by a polynucleotide comprising the sequence as shown in SEQ ID NO:6. In yet another preferred embodiment, the phenol oxidizing enzyme is encoded by the polynucleotide comprising the sequence as shown in SEQ ID NO:8. As will be understood by the skilled artisan, due to the degeneracy of the genetic code, a variety of polynucleotides can encode the phenol oxidizing enzyme disclosed in SEQ ID NO:4, SEQ ID NO:7 and SEQ ID NO:9. The present invention encompasses all such polynucleotides.

The nucleic acid encoding a phenol oxidizing enzyme may be obtained by standard procedures known in the art from, for example, cloned DNA (e.g., a DNA "library"), by chemical synthesis, by cDNA cloning, by PCR, or by the cloning of genomic DNA, or fragments thereof, purified from a desired cell, such as a Biopolaris species, Curvularia species or Amerosporium species (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.). Nucleic acid sequences derived from genomic DNA may contain regulatory regions in addition to coding regions. Whatever the source, the isolated nucleic acid encoding a phenol oxidizing enzyme of the present invention should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis, PCR and column chromatography.

Once nucleic acid fragments are generated, identification of the specific DNA fragment encoding a phenol oxidizing enzyme may be accomplished in a number of ways. For example, a phenol oxidizing enzyme encoding gene of the present invention or its specific RNA, or a fragment thereof, such as a probe or primer, may be isolated and labeled and then used in hybridization assays to detect a generated gene. (Benton, W. and Davis, R., 1977, Science 196:180; Grunstein, M. And Hogness, D., 1975, Proc. Natl. Acad. Sci. USA 72:3961). Those DNA fragments sharing substantial sequence similarity to the probe will hybridize under stringent conditions.

The present invention encompasses phenol oxidizing enzymes encoded by nucleic acid identified through nucleic acid hybridization techniques using SEQ ID NO:1 as a probe or primer and screening nucleic acid of either genomic or cDNA origin. Nucleic acid encoding phenol oxidizing enzymes obtainable from bacteria, yeast or non-Stachybotrys fungal species and having at least 60% identity to SEQ ID NO:1 can be detected by DNA—DNA or DNA-RNA hybridization or amplification using probes, portions or fragments of SEQ ID NO:1. Accordingly, the present invention provides a method for the detection of nucleic acid encoding a phenol oxidizing enzyme encompassed by the present invention which comprises hybridizing part or all of a nucleic acid sequence of SEQ ID NO:1 with Stachybotrys nucleic acid of either genomic or cDNA origin.

Also included within the scope of the present invention are polynucleotide sequences that are capable of hybridizing to the nucleotide sequence disclosed in SEQ ID NO:1 under conditions of intermediate to maximal stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego, Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. For example in the present invention the following are the conditions for high stringency: hybridization was done at 37° C. in buffer containing 50% formamide, 5×SSPE, 0.5% SDS and 50 ug/ml of sheared Herring DNA. The washing was performed at 65° C. for 30 minutes in the presence of 1×SSC and 0.1% SDS once, at 65° C. for 30 minutes in presence of 0.5×SSC and 0.1% SDS once and at 65° C. for 30 minutes in presence of 0.1×SSC and 0.1% SDS once; the following are the conditions for intermediate stringency: hybridization was done at 37° C. in buffer containing 25% formamide, 5×SSPE, 0.5% SDS and 50 ug/ml of sheared Herring DNA. The washing was performed at 5° C. for 30 minutes in presence of 1×SSC and 0.1% SDS once, at 5° C. for 30 minutes in presence of 0.5×SSC and 0.1% SDS once; the following are the conditions for low stringency: hybridization was done at 37° C. in buffer containing 25% formamide, 5×SSPE, 0.5% SDS and 50 ug/ml of sheared Herring DNA. The washing was performed at 37° C. for 30 minutes in presence of 1×SSC and 0.1% SDS once, at 37° C. for 30 minutes in presence of 0.5×SSC and 0.1% SDS once. A nucleic acid capable of hybridizing to a nucleic acid probe under conditions of high stringency will have about 80% to 100% identity to the probe; a nucleic acid capable of hybridizing to a nucleic acid probe under conditions of intermediate stringency will have about 50% to about 80% identity to the probe.

The term "hybridization" as used herein shall include "the process by which a strand of nucleic acid joins with a complementary strand through base pairing" (Coombs J (1994) Dictionary of Biotechnology, Stockton Press, New York, N.Y.).

The process of amplification as carried out in polymerase chain reaction (PCR) technologies is described in Dieffenbach C W and G S Dveksler (1995, PCR Primer, a Laboratory Manual, Cold Spring Harbor Press, Plainview, N.Y.). A nucleic acid sequence of at least about 10 nucleotides and as many as about 60 nucleotides from SEQ ID NO:1 preferably about 12 to 30 nucleotides, and more preferably about 25 nucleotides can be used as a probe or PCR primer.

A preferred method of isolating a nucleic acid construct of the invention from a cDNA or genomic library is by use of polymerase chain reaction (PCR) using oligonucleotide probes prepared on the basis of the polynucleotide sequence as shown in SEQ ID NO:1. For instance, the PCR may be carried out using the techniques described in U.S. Pat. No. 4,683,202.

Expression Systems

The present invention provides host cells, expression methods and systems for the production of phenol oxidizing enzymes obtainable from bacteria, yeast or non-Stachybotrys fungal species in host microorganisms. Such host microorganisms include fungus, yeast and bacterial species. Once nucleic acid encoding a phenol oxidizing enzyme of the present invention is obtained, recombinant host cells containing the nucleic acid may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989). Nucleic acid encoding a phenol oxidizing enzyme of the present invention is obtained and transformed into a host cell using appropriate vectors. A variety of vectors and transformation and expression cassettes suitable for the cloning, transformation and expression in fungus, yeast and bacteria are known by those of skill in the art.

Typically, the vector or cassette contains sequences directing transcription and translation of the nucleic acid, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the phenol oxidizing enzymes in a host cell are known to those skilled in the art. Virtually any promoter capable of driving these phenol oxidizing enzyme is suitable for the present invention. Nucleic acid encoding the phenol oxidizing enzyme is linked operably through initiation codons to selected expression control regions for effective expression of the enzymes. Once suitable cassettes are constructed they are used to transform the host cell.

General transformation procedures are taught in Current Protocols In Molecular Biology (vol. 1, edited by Ausubel et al., John Wiley & Sons, Inc. 1987, Chapter 9) and include calcium phosphate methods, transformation using PEG and electroporation. For Aspergillus and Trichoderma, PEG and Calcium mediated protoplast transformation can be used (Finkelstein, DB 1992 Transformation. In Biotechnology of Filamentous Fungi. Technology and Products (eds by Finkelstein & Bill) 113–156. Electroporation of protoplast is disclosed in Finkelestein, DB 1992 Transformation. In Biotechnology of Filamentous Fungi. Technology and Products (eds by Finkelstein & Bill) 113–156. Microprojection bombardment on conidia is described in Fungaro et al. (1995) Transformation of Aspergillus nidulans by microprojection bombardment on intact conidia. FEMS Microbiology Letters 125 293–298. Agrobacterium mediated transformation is disclosed in Groot et al. (1998) *Agrobacterium tumefaciens*-mediated transformation of filamentous fungi. Nature Biotechnology 16 839–842. For transformation of Saccharomyces, lithium acetate mediated transformation and PEG and calcium mediated protoplast transformation as well as electroporation techniques are known by those of skill in the art.

Host cells which contain the coding sequence for a phenol oxidizing enzyme of the present invention and express the protein may be identified by a variety of procedures known to those of skill in the art. These procedures include, but are not limited to, DNA—DNA or DNA-RNA hybridization and protein bioassay or immunoassay techniques which include membrane-based, solution-based, or chip-based technologies for the detection and/or quantification of the nucleic acid or protein.

Phenol Oxidizing Enzyme Activities

The phenol oxidizing enzymes of the present invention are capable of using a wide variety of different phenolic compounds as electron donors, while being very specific for molecular oxygen as the electron acceptor and/or hydrogen peroxide as the electron acceptor.

Depending upon the specific substrate and reaction conditions, e.g., temperature, presence or absence of enhancers, etc., each phenol oxidizing enzyme oxidation reaction will have an optimum pH.

The phenol oxidizing enzymes of the present invention are capable of oxidizing a wide variety of dyes or colored compounds having different chemical structures, using oxygen and/or hydrogen peroxide as the electron acceptor. Accordingly phenol oxidizing enzymes of the present invention are used in applications where it is desirable to modify the color associated with dyes or colored compounds, such as in cleaning, for removing the food stains on fabric and anti-dye redeposition; textiles; and paper and pulp applications.

Colored Compounds

In the present invention, a variety of colored compounds could be targets for oxidation by phenol oxidizing enzymes of the present invention. For example, in detergent applications, colored substances which may occur as stains on fabrics can be a target. Several types or classes of colored substances may appear as stains, such as porphyrin derived structures, such as heme in blood stain or chlorophyll in plants; tannins and polyphenols (see P. Ribéreau-Gayon, Plant Phenolics, Ed. Oliver & Boyd, Edinburgh, 1972, pp.169–198) which occur in tea stains, wine stains, banana stains, peach stains; carotenoids, the coloured substances which occur in tomato (lycopene, red), mango (carotene, orange-yellow) (G. E. Bartley et al., The Plant Cell (1995), Vol 7, 1027–1038); anthocyanins, the highly colored molecules which occur in many fruits and flowers (P. Ribéreau-Gayon, Plant Phenolics, Ed. Oliver & Boyd, Edinburgh, 1972, 135–169); and Maillard reaction products, the yellow/brown colored substances which appear upon heating of mixtures of carbohydrate molecules in the presence of protein/peptide structures, such as found in cooking oil. Pigments are disclosed in Kirk-Othmer, Encyclopedia of Chemical Technology, Third edition Vol. 17; page 788–889, a Wiley-Interscience publication. John Wiley & Sons and dyes are disclosed in Kirk-Othmer, Encyclopedia of Chemical Technology, Third edition,vol. 8, a Wiley-interscience publication. John Wiley & Sons.

Enhancers

A phenol oxidizing enzyme of the present invention may act to modify the color associated with dyes or colored compounds in the presence or absence of enhancers depending upon the characteristics of the compound. If a compound is able to act as a direct substrate for the phenol oxidizing enzyme, the phenol oxidizing enzyme can modify the color associated with a dye or colored compound in the absence of an enhancer, although an enhancer may still be preferred for optimum phenol oxidizing enzyme activity. For other colored compounds unable to act as a direct substrate for the phenol oxidizing enzyme or not directly accessible to the phenol oxidizing enzyme, an enhancer is required for optimum phenol oxidizing enzyme activity and modification of the color.

Enhancers are described in for example WO 95/01426 published Jan. 12, 1995; WO 96/06930, published Mar. 7, 1996; and WO 97/11217 published Mar. 27, 1997. Enhancers include but are not limited to phenothiazine-10-propionic acid (PPT), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'-azino-bis (3-ethylbenzothiazoline-6-sulfonate (ABTS) and 4-Hydroxy-4-biphenyl-carboxylic acid.

Cultures

The present invention encompasses phenol oxidizing enzymes obtainable from fungus including but not limited to Myrothecium species, Curvalaria species, Chaetomium species, Bipolaris species, Humicola species, Pleurotus species, Trichoderma species, Mycellophthora species and Amerosporium species. In particular, the fungus includes but is not limited to *Myrothecium verrucaria*, *Curvalaria pallescens*, Chaetomium sp, *Bipolaris spicifera*, *Humicola insolens*, *Pleurotus abalonus*, *Trichoderma reesei*, *Mycellophthora thermophila* and *Amerosporium atrum*. In addition to the illustrative examples provided herein, other examples of the above species include *Myrothecium verrucaria* having ATCC accession number 36315; *Pleurotus abalonus* having ATCC accession number 96053; *Humicola insolens* having ATCC accession number 22082; *Mycellophthora thermophila* having ATCC accession number 48104; and *Trichoderma reesei* having ATCC Accession Number 56765.

Purification

The phenol oxidizing enzymes of the present invention may be produced by cultivation of phenol oxidizing enzyme-producing strains under aerobic conditions in nutrient medium containing assimiable carbon and nitrogen together with other essential nutrient(s). The medium can be composed in accordance with principles well-known in the art.

During cultivation, the phenol oxidizing enzyme-producing strains secrete phenol oxidizing enzyme extracellularly. This permits the isolation and purification (recovery) of the phenol oxidizing enzyme to be achieved by, for example, separation of cell mass from a culture broth (e.g. by filtration or centrifugation). The resulting cell-free culture broth can be used as such or, if desired, may first be concentrated (e.g. by evaporation or ultrafiltration). If desired, the phenol oxidizing enzyme can then be separated from the cell-free broth and purified to the desired degree by conventional methods, e.g. by column chromatography, or even crystallized.

The phenol oxidizing enzymes of the present invention may be isolated and purified from the culture broth into which they are extracellularly secreted by concentration of the supernatant of the host culture, followed by ammonium sulfate fractionation and gel permeation chromatography. As described herein in Example I for *Stachybotrys chartarum* phenol oxidizing enzyme, the phenol oxidizing enzymes of the present invention may be purified and subjected to standard techniques for protein sequencing, Oligonucleotide primers can be designed based on the protein sequence and used in PCR to isolate the nucleic acid encoding the phenol oxidizing enzyme. The isolated nucleic acid can be characterized and introduced into host cells for expression. Accordingly, the present invention encompasses expression vectors and recombinant host cells comprising a phenol oxidizing enzyme of the present invention and the subsequent purification of the phenol oxidizing enzyme from the recombinant host cell.

The phenol oxidizing enzymes of the present invention may be formulated and utilized according to their intended application. In this respect, if being used in a detergent composition, the phenol oxidizing enzyme may be formulated, directly from the fermentation broth, as a coated solid using the procedure described in U.S. Pat. No. 4,689, 297. Furthermore, if desired, the phenol oxidizing enzyme may be formulated in a liquid form with a suitable carrier. The phenol oxidizing enzyme may also be immobilized, if desired.

Assays for Phenol Oxidizing Activity

Phenol oxidizing enzymes can be assayed for example by ABTS activity as described in Example II or by the delignification method as disclosed in Example III or in detergent methods known by those of skill in the art.

Detergent Compositions

A phenol oxidizing enzyme of the present invention may be used in detergent or cleaning compositions. Such compositions may comprise, in addition to the phenol oxidizing enzyme, conventional detergent ingredients such as surfactants, builders and further enzymes such as, for example, proteases, amylases, lipases, cutinases, cellulases or peroxidases. Other ingredients include enhancers, stabilizing agents, bactericides, optical brighteners and perfumes. The detergent compositions may take any suitable physical form, such as a powder, an aqueous or non aqueous liquid, a paste or a gel. Examples of detergent compositions are given in WO 95/01426, published Jan. 12, 1995 and WO 96/06930 published Mar. 7, 1996.

Having thus described the phenol oxidizing enzymes of the present invention, the following examples are now presented for the purposes of illustration and are neither meant to be, nor should they be, read as being restrictive. Dilutions, quantities, etc. which are expressed herein in terms of percentages are, unless otherwise specified, percentages given in terms of per cent weight per volume (w/v). As used herein, dilutions, quantities, etc., which are expressed in terms of % (v/v), refer to percentage in terms of volume per volume. Temperatures referred to herein are given in degrees centigrade (C). All patents and publications referred to herein are hereby incorporated by reference.

EXAMPLE I

*Stachybotrys chartarum* phenol oxidizing enzyme production

*Stachybotrys chartarum* ATCC accession number 38898 was grown on PDA plates (Difco) for about 5–10 days. A portion of the plate culture (about ¾x¾ inch) was used to inoculate 100 ml of PDB (potato dextrose broth) in 500-ml shake flask. The flask was incubated at 26–28 degrees C, 150 rpm, for 3–5 days until good growth was obtained.

The broth culture was then inoculated into 1 L of PDB in a 2.8-L shake flask. The flask was incubated at 26–28 degrees C, 150 rpm, for 2–4 days until good growth was obtained.

A 10-L fermentor containing a production medium was prepared (containing in grams/liter the following components: glucose 15; lecithin1.51; t-aconitic acid 1.73; KH2PO4 3; MgSO4.7H2O 0.8; CaCl2.2H2O 0.1; ammonium tartrate 1.2; soy peptone 5; Staley 7359; benzyl alcohol 1; tween 20 1; nitrilotriacetic acid 0.15; MnSO4.7H2O 0.05; NaCl 0.1; FeSO4.7H2O 0.01; CoSO4 0.01; CaCl2.2H2O 0.01; ZnSO4.7H2O 0.01; CuSO4 0.001; ALK(SO4) 2.12H2O 0.001; H3BO3 0.001; NaMoO4.2H2O 0.001). The fermentor was then inoculated with the 1-L broth culture, and fermentation was conducted at 28 degrees C for 60 hours, under a constant air flow of 5.0 liters/minute and a constant agitation of 120 RPM. The pH was maintained at 6.0.

The presence of phenol oxidizing enzyme activity in the supernatant was measured using the following assay procedure, based on the oxidation of ABTS (2,2'-azino-bis-(3-ethylbenzothiazoline-6-sulfonate)) by oxygen. ABTS (SIGMA, 0.2 ml, 4.5 mM H2O) and NaOAc (1.5 ml, 120 mM in H2O, pH 5.0) were mixed in a cuvette. The reaction was started by addition of an appropriate amount of the preparation to be measured (which in this example is the supernatant dilution) to form a final solution of 1.8 ml. The color produced by the oxidation of ABTS was then measured every 2 seconds for total period of 14 seconds by recording the optical density (OD) at 420 nm, using a spectrophotometer. One ABTS unit (one enzyme unit or EACU) in this example is defined as the change in OD measured at 420 per minute/2 (given no dilution to the sample). In this manner a phenol oxidizing enzyme activity of 3.5 EACU/ml of culture supernatant was measured.

The resulting supernatant was then removed from the pellet and concentrated to 0.6 liters by ultrafiltration using a Amicon ultrafiltration unit equipped with a YMI0 membrane having a 10 kD cutoff.

A volume of 1.4 liters of acetone was added to the concentrate and mixed therewith. The resulting mixture was then incubated for two hours at 20–25 degrees C.

Following incubation, the mixture was centrifuged for 30 minutes at 10,000 g and the resulting pellet was removed from the supernatant. The pellet was then resuspended in a final volume of 800 ml of water.

The resulting suspension was then submitted to ammonium sulfate fractionation as follows: crystalline ammonium sulfate was added to the suspension to 40% saturation and the mixture incubated at 4 degrees C for 16 hours with gentle magnetic stirring. The mixture was then centrifuged at 10,000 g for 30 minutes and the supernatant removed from the centrifugation pellet for further use. Ammonium sulfate was then added to the supernatant to reach 80% saturation, and the mixture incubated at 4 degrees C for 16 hours with gentle magnetic stirring. The suspension was then centrifuged for 30 minutes at 10,000 g and the resulting pellet was removed from the supernatant. The pellet was then resuspended in 15 ml of water and concentrated to 6 ml by ultrafiltration using a CENTRIPREP 3000 (AMICON).

The phenol oxidizing enzyme activity of the suspension was then measured using the standard assay procedure, based on the oxidation of ABTS by oxygen, as was described above (but with the exception that the preparation being assayed is the resuspended concentration and not the supernatant dilutions). The phenol oxidizing enzyme activity so measured was 5200 EU/ml.

The enzyme was then further purified by gel permeation chromatography. In this regard, a column containing 850 ml of SEPHACRYL S400 HIGH RESOLUTION (PHARMACIA) was equilibrated with a buffer containing 50 mM KH2PO4/K2HPO4 (pH=7.0) and then loaded with the remainder of the 6 ml suspension described above, and eluted with the buffer containing 50 mM KH2PO4/K2HPO4 (pH=7.0), at a flow rate of 1 ml/minute. Respective fractions were then obtained.

The respective fractions containing the highest phenol oxidizing enzyme activities were pooled together, providing a 60 ml suspension containing the purified phenol oxidizing enzyme.

The phenol oxidizing enzyme activity of the suspension was then measured based on the oxidation of ABTS by oxygen. The enzyme activity so measured was 390 EU/ml. *Stachybotrys chartarum* phenol oxidizing enzyme prepared as disclosed above was subjected to SDS polyacrylamide gel electrophoresis and isolated. The isolated fraction was treated with urea and iodoacetamide and digested by the enzyme endoLysC. The fragments resulting from the endoLysC digestion were separated via HPLC (reverse phase monobore C18 column, CH3CN gradient) and collected in a multititer plate. The fractions were analysed by MALDI for mass determination and sequenced via Edman degradation. The following amino acid sequences were determined and are shown in amino terminus to carboxy terminus orientation:

N' DYYFPNYQSARLLXYHDHA C' (SEQ ID NO: 10)
N' RGQVMPYESAGLK C' (SEQ ID NO: 11)

Two degenerated primers were designed based on the peptide sequence. Primer 1 contained the following sequence: TATTACTTTCCNAAYTAYCA (SEQ ID NO: 12) where N represents a mixture of all four nucleotides (A, T, C and G) and Y represents a mixture of T and C only. Primer 2 contained the following sequence:

TCGTATGGCATNACCTGNCC (SEQ ID NO: 13).

For isolation of genomic DNA encoding phenol oxidizing enzyme, DNA isolated from *Stachybotrys chartarum* (MUCL # 38898) was used as a template for PCR. The DNA was diluted 100 fold with Tris-EDTA buffer to a final concentration of 88 ng/ul. Ten microliter of diluted DNA was added to the reaction mixture which contained 0.2 mM of each nucleotide (A, G. C and T), 1× reaction buffer, 0.296 microgram of primer 1 and 0.311 microgram of primer 2 in a total of 100 microliter reaction. After heating the mixture at 100° C. for 5 minutes, 2.5 units of Taq DNA polymerase was added to the reaction mix. The PCR reaction was performed at 95° C. for 1 minute, the primers were annealed to the template at 45° C. for 1 minute and extension was done at 68 ° C. for 1 minute. This cycle was repeated 30 times to achieve a gel-visible PCR fragment. The PCR fragment detected by agarose gel contained a fragment of about 1 kilobase which was then cloned into the plasmid vector pCR-II (Invitrogen). The 1 kb insert was then subjected to nucleic acid sequencing. The sequence data revealed that it was the gene encoding *Stachybotrys chartarum* because the deduced peptide sequence matched the peptide sequences disclosed above sequenced via Edman degradation. The PCR fragments containing the 5' gene and 3' gene were then isolated and sequenced. FIG. 1 provides the full length genomic sequence (SEQ ID NO:1) of Stachybotrys oxidase including the promoter and terminator sequences.

EXAMPLE II

The following example describes the ABTS assay used for the determination of phenol oxidizing activity. The ABTS assay is a spectrophotometric activity assay which uses the following reagents: assay buffer=50 sodium acetate, pH 5.0; 50 mM sodium phosphate, pH 7.0; 50 mM sodium carbonate, pH 9.0. The ABTS (2,2'-azinobis 3 ethylbenzothiazoline-6-sulphonic acid]) is a 4.5 mM solution in distilled water.

0.75 ml assay buffer and 0.1 ml ABTS substrate solution are combined, mixed and added to a cuvette. A cuvette containing buffer-ABTS solution is used as a blank control. 0.05 ml of enzyme sample is added, rapidly mixed and placed into the cuvette containing buffer-ABTS solution. The rate of change in absorbance at 420 nm is measure, DOD 420/minute, for 15 seconds (or longer for samples having activity rates<0.1) at 30° C. Enzyme samples having a high rate of activity are diluted with assay buffer to a level between 0.1 and 1.

EXAMPLE III

In this example a shake flask pulp bleaching protocol was used to determine the activity of phenol oxidizing enzymes.

The buffer used is 50 mM Na Acetate, pH 5 or 50 mM Tris pH 8.5. Softwood, oxygen delignified pulp with a of kappa 17.3 is used. The enzyme is dosed at 10 ABTS units per g of pulp. The assay can be performed with and without mediators, such as those described infra.

250 ml of pre-warmed buffer is placed in a graduated cylinder. 10 g of wet pulp (at 72% moisture=2.8 g dry pulp) is placed into a standard kitchen blender with ~120 ml buffer. The pulp is blended on the highest setting for about 30 seconds. The resulting slurry is placed into a large-mouth shake flask (residual pulp is rinsed out of the blender with remaining buffer and spatula) which results in about a 1% consistency in the flask (2.8 g/250 ml).

The enzyme +/− mediator is added and controls without enzyme are included in the assay. The opening of the flask is covered with 2 thickness cheese cloth and secured with a rubber band. The flasks are placed into a shaker and incubated for 2 hours at ~55° C. and 350 rpm.

At the end of the incubation time, 500 mls of 2% NaOH are added directly into the flasks and the shaker temperature is set to 70° C. and allowed to incubate for 1.5 hours at 250 rpm. The flask contents are filtered through buchner funnels. The pulp slurries are poured directly into the funnels, without vacuum and are allowed to slowly drip which sets up a filter layer inside the funnel.

Once most of the flask contents are in the funnel, a light vacuum is applied to pull the material into a cake inside the funnel. The filtrate (liquid) is poured back into the original shake flask and swirled to wash residual pulp from the sides. The filtrate is poured back on top of the filter cake. The end result is a fairly clear light golden colored filtrate with most of the pulp caught in the funnel. The filter cake is washed without vacuum, by gently pouring 1 liter of Dl water over the filter cake and letting it drip through on its own. A vacuum is applied only at the end to suck the cake dry. The filter cakes are dried in the funnels overnight in a 100° C. oven. The dried pulp is manually scraped from the cooled funnels the next day. Microkappa determinations based on the method of the Scandinavian Pulp, Paper and Board Testing committee Scan-c 1:77 (The Scandinavian Pulp, Paper and Board Testing committee Box 5604,S-114, 86 Stockholm, Sweden) are performed to determine % delignification.

EXAMPLE IV

Example IV describes the Southern hybridization technique used to identify homologous genes from other organisms.

The genomic DNA from several fungal strains including the *Stachybotrys chartarum, Myrothecium verruvaria, Myrothecium cinctum, Curvalaria pallescens, Humicola insolens, Pleurotus eryngii, Pleurotus abalous, Aspergillus niger, Corpinus cineras, Mycellophthora thermophila, Trichoderma reesei, Trametes vesicolor*, Chaetomium sp, and *Bipolaris spicifera* was isolated. All fungal species were grown in either CSL medium (described in Dunn-Coleman et al., 1991, Bio/Technology 9:976–981) or MB medium (glucose 40 g/l; soytone 10 g/l; MB trace elements 1 ml/L at pH 5.0) for 2 to 4 days. The mycelia were harvested by filtering through Mirocloth (Calbiochem). The genomic DNA was extracted from cells by repeated phenol/chloroform extraction according to the fungal genomic DNA purification protocol (Hynes M J, Corrick C M, King J A 1983, Mol Cell Biol 3:1430–1439). Five micrograms genomic DNA were digested with restriction enzyme EcoRI or Hind III overnight at 37° C. and the DNA fragments were separated on 1% agarose gel by electrophoresis in TBE buffer. The DNA fragments were then transferred from agarose gel to the Nitrocellulose membrane in 20×SSC buffer. The probe used for Southern analysis was isolated from plasmids containing either the entire coding region of the Stachybotrys phenol oxidizing enzyme (SEQ ID NO:1) or a DNA fragment generated through PCR reaction that covers the internal part of the genes of more than 1 kb in size. The primers used to generate the PCR fragment were Primer 1 containing the following sequence: TATTACTTTCCNAAYTAYCA (SEQ ID NO: 12) where N represents a mixture of all four nucleotides (A, T, C and G) and Y represents a mixture of T and C only and Primer 2 containing the following sequence: TCGTATGGCATNACCTGNCC (SEQ ID NO: 13). Southern hybridizations were performed for 18 to 20 hours at 37 ° C. in an intermediate stringency hybridization buffer containing 25% formamide, 5×SSPE, 0.5% SDS and 50 ug/ml of sheared Herring DNA. The blots were washed once at 50° C. for 30 minutes in presence of 1×SSC and 0.1% SDS and washed again at 50° C. for 30 minutes in 0.5×SSC and 0.1% SDS. The Southern blots were exposed to x-ray film for more than 20 hours and up to 3 days. FIGS. 6, 7, and 8 show that the genomic DNAs of several fungal species contained sequences that were able to hybridize under the conditions described above to the nucleic acid encoding the Stachybotrys phenol oxidizing enzyme shown in SEQ ID NO:1. These fungal species giving the strongest signal (which may indicate a higher identity to the nucleic acid probe than those giving a weaker signal) are *Myrothecium verrucaria, Curvalaria pallescens*, Chaetomium sp, *Bipolaris spicifera*, and *Amerosporium atrum*. Fungal species also hybridizing to nucleic acid encoding the Stachybotrys phenol oxidizing enzyme were detected from genomic DNA of *Humicola insolens, Pleurotus abalonus, Trichoderma reesei* and *Mycellophthora thermophila*.

EXAMPLE V

Example V describes the cloning of genes encoding fungal enzymes capable of hybridizing to Stachybotrys phenol oxidizing enzyme of SEQ ID NO:1.
A. *Bipolaris spicifera*

Based on the DNA and protein sequences comparison of the phenol oxidizing enzyme of SEQ ID NO:1 (from the *Stachybotrys chartarum*) and bilirubin oxidase from the *Myrothecium verruvaria* (GenBank number 14081), a set of oligonucleotide primers was designed to isloate related sequences from a number of different organisms via hybridization techniques. The following oligonucleotide primers (primer 1:5' TGGTACCAYGAYCAYGCT 3' (SEQ ID NO:14) and primer 2:5' RGACTCGTAKGGCATGAC 3' (SEQ ID NO:15) (where the Y is an equal mixture of nucleotides T and C, R is an equal mixture of nucleotides A and G and K represents an equal mixture of nucleotides T and G) were used to clone a phenol oxidizing enzyme from Bipolaris spicifera. The genomic DNA isolated from Bipolaris spicifera was diluted 10 fold with Tris-EDTA buffer to a final concentration of 63 ng/ul. Ten microliters of diluted DNA were added to a reaction mixture which contained 0.2 mM of each nucleotide (A, G. C and T), 1× reaction buffer (10 mM Tis, 1.5 mM MgCl2, 50 mM KCl at pH 8.3) in a total of 100 microliters reaction in the presence of primers 1 and 2. After heating the mixture at 100° C. for 5 minutes, 2.5 units of Taq DNA polymerase was added to the reaction mix. The PCR reaction was performed at 95° C. for 1 minute, the primer was annealed to the template at 50° C. for 1 minute and extension was done at 75° C. for 1 minute. This cycle was repeated 30 times to achieve a gel-visible PCR fragment and an extension at 72° C. for 7 minutes was added after 30 cycles. The PCR fragment detected by agarose gel contained a fragment of about 1 kilobase which was then cloned into the plasmid vector pCR-II (Invitrogen). The 1 kb insert was then subjected to nucleic acid sequencing. The 3' end of the gene was isolated by RS-PCR method (Sarkar et al., 1993, PCR Methods and Applications 2:318–322) from the genomic DNA of the *Bipolaris spicifera*. The PCR fragment was cloned into the plasmid vector pCR-II (Invitrogen) and sequenced. The 5' end of the gene was isolated by the same RS-PCR method (Sarkar et al 1993, PCR methods and applications 2:318–322) from the genomic DNA of the *Bipolaris spicifera*. The PCR fragment was also cloned into the plasmid vector pCR-II (Invitrogen) and sequenced. The full length genomic DNA (SEQ ID NO:3) including the regulatory sequence of the promoter and terminator regions is shown in FIG. 2 and the amino acid sequence translated from genomic DNA is shown in FIG. 3 (SEQ ID NO:4). The sequence data comparison, shown in FIG. 4, revealed that it encodes a phenol oxidizing enzyme having about 60.8% identity to the *Stachybotrys chartarum* phenol oxidizing enzyme shown in SEQ ID NO:2 (as determined by MegAlign Program from DNAstar (DNASTAR, Inc. Madison, Wis. 53715) by Jotun Hein Method (1990, Method in Enzymology, 183: 626–645) with a gap penalty=11, a gap length penalty=3 and Pairwise Alignment Parameters Ktuple=2.

B. *Curvularia pallescens*

Based on the comparison of the nucleic acid and protein sequences of the phenol oxidizing enzyme of SEQ ID NO:1 (obtainable from *Stachybotrys chartarum*) and bilirubin oxidase obtainable from *Myrothecium verruvaria* (GenBank accession number 14081), a set of oligonucleotide primers was designed to isolate related sequences from a number of different organisms via hybridization techniques. The following oligonucleotide primers (primer 1: 5' TGGTAC-CAYGAYCAYGCT 3' (SEQ ID NO: 14) and primer 2: 5' TCGTGGATGARRTTGTGRCAR 3' (SEQ ID NO: 16) (where the Y is an equal mixture of nucleotides T and C, R is an equal mixture of nucleotides A and G) were used to clone a phenol oxidizing enzyme from *Curvularia pallescens*. The genomic DNA isolated from *Curvularia pallescens* was diluted with Tris-EDTA buffer to a final concentration of 200 ng/ul. Ten microliters of diluted DNA were added to a reaction mixture which contained 0.2 mM of each nucleotide (A, G, C and T), 1× reaction buffer (10 mM Tris, 1.5 mM MgCl2, 50 mM KCl at pH 8.3) in a total of 100 microliters reaction in the presence of primers 1 and 2. After heating the mixture at 100° C. for 5 minutes, 2.5 units of Taq DNA polymerase were added to the reaction mix. The PCR reaction was performed at 95° C. for 1 minute, the primer was annealed to the template at 50° C. for 1 minute and extension was done at 72° C. for 1 minute. This cycle was repeated 30 times and an extension at 72° C. for 7 minutes was added after 30 cycles. The PCR fragment detected by agarose gel contained a fragment of about 900 base pairs. The 900 bp PCR fragment was then subjected to nucleic acid sequencing. The 5' and part of 3' end of the genomic DNA was isolated by inverse PCR method (Triglia T et al, Nucleic Acids Res. 16:8186) from the genomic DNA of *Curvularia pallescens* using two pairs of oligonucleotides based on sequence data from the 900 bp PCR fragment. The full length genomic DNA (SEQ ID NO:6) from the translation start site to the translation stop site is shown in FIG. 9 and the putative amino acid sequence translated from genomic DNA is shown in FIG. 10 (SEQ ID NO:7) The sequence data comparison, shown in FIG. 11, illustrates that the phenol oxidizing enzyme obtainable from *Curvalaria pallescens* and having SEQ ID NO:7 has 92.8% identity to the phenol oxidizing enzyme cloned from *Bipolaris spicifera* shown in SEQ ID NO:4 (as determined by MegAlign Program from DNAstar (DNASTAR, Inc. Madison, Wis. 53715) by Jotun Hein Method (1990, Method in Enzymology, 183: 626–645) with a gap penalty=11, a gap length penalty=3 and Pairwise Alignment Parameters Ktuple=2. SEQ ID NO:7 has 60.8% identity to the Stachybotrys oxidase phenol oxidizing enzyme A shown in SEQ ID NO: 2.

C. *Amerosparium atrum*

Based on the DNA and protein sequences comparison of the phenol oxidizing enzyme of SEQ ID NO:1 (from the *Stachybotrys chartarum*) and bilirubin oxidase from the *Myrothecium verruvaria* (GenBank number 14081), a set of oligonucleotide primers was designed to isolate related sequences from a number of different organisms via hybridization techniques. The following oligonucleotide primers (primer 1:5' TGGTACCAYGAYCAYGCT 3' (SEQ ID NO: 14) and primer 2:5' CXAGACRACRTCYTTRAGACC 3' (SEQ ID: 17) (where the Y is an equal mixture of nucleotides T and C, R is an equal mixture of nucleotides A and G and X is an equal mixture of nucleotides G, A, T and C) were used to clone a phenol oxidizing enzyme from *Amerosporium atrum*. A reaction mixture which contained 0.2 mM of each nucleotide (A, G. C and T), 1× reaction buffer (10 mM tris, 1.5 mM MgCl2, 50 mM KCl at pH 8.3), 1 ul of 50 pmol/ul primers 1 and 2 in a total of 50 microliters reaction were added to a hot start tube (Molecular Bio-Products). The mixture was heated to 95° C. for 90 seconds, and the tubes were cooled on ice for 5 minutes. The genomic DNA isolated from Amerosporium atrum was diluted 10 fold with Tris-EDTA buffer to a final concentration of 41 ng/ul. About 1 ul of the diluted DNA was added to hot start tube with 1× reaction buffer (10 mM Tris, 1.5 mM MgCl2, 50 mM KCl at pH 8.3), 2.5 units of Taq DNA polymerase in a total volume to 50 microliters. The reaction mixture was heated to 95° C. for 5 minutes. The PCR reaction was performed at 95° C. for 1 minute, the primer was annealed to the template at 51° C. for 1 minute and extension was done at 72° C. for 1 minute. This cycle was repeated 29 times to achieve a gel-visible PCR fragment and an extension at 72° C. for 7 minutes was added after 29 cycles. The PCR fragment detected by agarose gel contained a fragment of about 1 kilobase. The 1 kb insert was then subjected to nucleic acid sequencing. The genomic sequence for the *Amerosporium atrum* is shown in FIG. 13. An amino acid alignment of the amino acid obtainable from *Amerosporium atrum* and SEQ ID NO: 2 is shown in FIG. 14.

EXAMPLE VI

Example VI illustrates the *Bipolaris spicifera* pH profile as measured at 470 nm using Guaicol as a substrate.

Phenol oxidizing enzyme obtainable from *Bipolaris spicifera* was diluted in water and added to 96 well plates which contained the Briton and Robinson buffer system at a final concentration of 20 mM. Guaicol (Sigma catalog number 6-5502) was added to the wells at a final concentration of 1 mM. The reaction was allowed to proceed for 15' at a temperature of 25° C. and a reading was taken every 11 minutes using a spectrophotometer at a lambda of 470 nm. The results are shown in FIG. 12.

The Briton and Robinson buffer system is shown in Table 1 below.

TABLE 1 x mL of 0.2M NaOH Added to 100 mL of Stock Solution (0.04M Acetic Acid, 0.04M H$_3$PO$_4$, and 0.04M Boric Acid)

| pH | NaOH, mL | pH | NaOH, mL | pH | NaOH, mL | pH | NaOH, mL |
|---|---|---|---|---|---|---|---|
| 1.81 | 0.0 | 4.10 | 25.0 | 6.80 | 50.0 | 9.62 | 75.0 |
| 1.89 | 2.5 | 4.35 | 27.5 | 7.00 | 52.5 | 9.91 | 77.5 |
| 1.98 | 5.0 | 4.56 | 30.0 | 7.24 | 55.0 | 10.38 | 80.0 |
| 2.09 | 7.5 | 4.78 | 32.5 | 7.54 | 57.5 | 10.88 | 82.5 |
| 2.21 | 10.0 | 5.02 | 35.0 | 7.96 | 60.0 | 11.20 | 85.0 |
| 2.36 | 12.5 | 5.33 | 37.5 | 8.36 | 62.5 | 11.40 | 87.5 |
| 2.56 | 15.0 | 5.72 | 40.0 | 8.69 | 65.0 | 11.58 | 90.0 |
| 2.87 | 17.5 | 6.09 | 42.5 | 8.95 | 67.5 | 11.70 | 92.5 |
| 3.29 | 20.0 | 6.37 | 45.0 | 9.15 | 70.0 | 11.82 | 95.0 |
| 3.78 | 22.5 | 6.59 | 47.5 | 9.37 | 72.5 | 11.92 | 97.5 |

EXAMPLE VII

Example VII illustrates the bleaching of tomato stains by phenol oxidizing enzyme obtainable from *Bipolaris spicifera* and comprising the sequence as shown in SEQ ID NO:4. The potential to bleach stains was assessed by washing cotton swatches soiled with tomato stains.

The experiments were performed in small 250 ml containers, to which 15 ml of wash solution were added (indicated in tables). The pH of the wash solution was set to pH 9. Purified phenol oxidizing enzyme obtainable from *Bipolaris spicifera* and having an amino acid sequence as shown in SEQ ID NO:4 was added to the wash solution at a concentration of 100 mg/l. Phenothiazine-10-propionate (PTP) was used as an enhancers, dosed at 250 $\mu$M. The following formulation was used as wash solution (2 gr/liter):

| Detergent Composition: | |
|---|---|
| LAS | 24% |
| STP | 14.5% |
| Soda ash | 17.5% |
| Silicate | 8.0% |
| SCMC | 0.37% |
| Blue pigment | 0.02% |
| Moisture/salts | 34.6% |

The swatches were washed during 30 minutes, at 30° C. After the wash, the swatches were tumble-dried and the reflectance spectra were measured using a Minolta spectrometer. The color differences between the swatch before and after the wash data were expressed in the CIELAB L*a*b* color space. In this color space, L* indicates lightness and a* and b* are the chromaticity coordinates. Color differences between two swatches are expressed as DE, which is calculated from the equation:

$$\Delta E = \sqrt{\Delta L^2 + \Delta a^2 + \Delta b^2}$$

The results, as $\Delta$E values, are shown in Table 2 below:

| Wash without bleach system | Wash with bleach system |
|---|---|
| $\Delta$E = 4.8 | $\Delta$E = 6.9 |

As can be seen from DE values, the bleaching of the tomato stain is improved in the presence of the enzyme/enhancer system.

We claim:

1. An isolated polynucleotide encoding the amino acid sequence comprising the sequence as shown in SEQ ID NO: 4.

2. The isolated polynucleotide of claim 1 comprising the nucleic acid sequence as disclosed in SEQ ID NO: 3.

3. An isolated polynucleotide encoding an oxidoreductase enzyme that hybridizes to the sequence shown in SEQ ID NO: 3 under conditions of intermediate stringency which includes hybridization at about 37° C. in buffer including 25% formamide and washing at about 50° C.

4. An expression vector comprising the polynucleotide of claim 1.

5. A host cell comprising the expression vector of claim 4.

6. The host cell of claim 5 that is a filamentous fungus.

7. The host cell of claim 6 wherein said filamentous fungus is selected from the group consisting of Aspergillus species, Trichoderma species, and Mucor species.

8. The host cell of claim 5 that is a yeast.

9. The host cell of claim 8 wherein said yeast is selected from the group consisting of Saccharomyces, Pichia, Schizosaccharomyces, Hansenula, Kluyveromyces, and Yarrowia species.

10. The host cell of claim 5 wherein said host is a bacterium.

11. The host cell of claim 10 wherein said bacterium is selected from the group consisting of Bacillus and Escherichia species.

12. A method for producing an oxidoreductase enzyme in a host cell comprising the steps of:
   a) obtaining a host cell comprising a polynucleotide that hybridizes to the nucleic acid shown in SEQ ID NO: 1 under conditions of intermediate stringency which includes hybridization at about 37° C. in buffer including 25% formamide and washing at about 50° C.; and
   b) growing said host cell under conditions suitable for the production of said oxidoreductase enzyme.

13. The method of claim 12 wherein said oxidoreductase enzyme comprises the amino acid sequence as disclosed in SEQ ID NO: 4.

14. The method of claim 12 wherein said polynucleotide comprises the sequence as shown in SEQ ID NO: 3.

15. A method for producing a host cell comprising an oxidoreductase enzyme comprising the steps of:
   a) obtaining a polynucleotide that hybridizes to the nucleic acid shown in SEQ ID NO: 1 under conditions of intermediate stringency which includes hybridization at about 37° C. in buffer including 25% formamide and washing at about 50° C.;
   b) introducing said polynucleotide into said host cell; and
   c) growing said host cell under conditions suitable for the production of said oxidoreductase enzyme.

16. The method of claim 15, wherein said polynucleotide comprises the nucleic acid sequence shown in SEQ ID NO: 3.

17. An expression vector comprising the polynucleotide of claim 14.

18. A host cell comprising the expression vector of claim 17.

19. The host cell of claim 18, wherein said host cell is a filamentous fungus.

20. The host cell of claim 18, wherein said host cell is a bacterium.

21. A method for producing an oxidoreductase enzyme in a host cell comprising the steps of:
   a) obtaining a host cell comprising a polynucleotide that hybridizes to the nucleic acid shown in SEQ ID NO: 1 under conditions of high stringency which includes hybridization at about 37° C. in buffer including 50% formamide and washing at about 65° C. wherein said polynucleotide is obtainable from a fungal genus other than the genus Stachybotrys; and
   b) growing said host cell under conditions suitable for the production of said oxidoreductase enzyme.

22. The method of claim 21, wherein said oxidoreductase enzyme has the amino acid sequence shown in SEQ ID NO: 4 or said oxidoreductase enzyme has an amino acid sequence having at least 85% sequence identity to SEQ ID NO: 4.

23. The method of claim 21, wherein said host cell is selected from the group consisting of filamentous fungus, yeast, and bacterium.

24. A method for producing a host cell comprising an oxidoreductase enzyme comprising the steps of:
   a) obtaining a polynucleotide that hybridizes to the nucleic acid shown in SEQ ID NO: 3 under conditions of intermediate stringency which includes hybridization at about 37° C. in buffer including 25% formamide and washing at about 50° C.;
   b) introducing said polynucleotide into the host cell; and
   c) growing said host cell under conditions suitable for the production of said oxidoreductase enzyme.

25. An isolated polynucleotide encoding an oxidoreductase enzyme comprising an amino acid sequence having at least 95% sequence identity to SEQ ID NO: 4 wherein said amino acid sequence is derived from a strain of *Bipolaris spicifera*.

26. A method for producing a host cell comprising an oxidoreductase enzyme comprising the steps of:
   a) obtaining a polynucleotide that hybridizes to the nucleic acid shown in SEQ ID NO: 3 under conditions of high stringency which includes hybridization at about 37° C. in buffer including 50% formamide and washing at about 65° C.;
   b) introducing said polynucleotide into said host cell; and
   c) growing said host cell under conditions suitable for the production of said oxidoreductase enzyme.

* * * * *

SEQUENCE LISTING

<160> NUMBER OF SEQ ID NOS: 17

<210> SEQ ID NO 1
<211> LENGTH: 3677
<212> TYPE: DNA
<213> ORGANISM: Stachybotrys chartarum

<400> SEQUENCE: 1

```
ctggctagcc tcacttggta gacagccctg acagcctcac tggctggggg tcgaaaggcc     60
agtcaatatc ttggtcactg ctaatagttc cttgctacgc gcaaaaagct ccttgccgaa    120
ggggcacaga ctatcaagtg agacatatag gatgcatgtc tttcatagcc acagttaggg    180
tggtgaccta ctcgaagagg ccccgacttg catgcatacg acatgtcgct tccatgcaac    240
atgtatgcgc acatcggcga tcaggcaccc tctgcatgca gaatagaacc cccctggttt    300
ccttttgttt cttttccttt ctcaacgacg cgtgagcgtg gttaacttga gcaaggccga    360
gtggtctgtt cacgaggtta ccatcgaact ctcttctttc ccaatcatga cctgcccccc    420
gagtttagcc cccatcacgg ctgtgaaatc cacttcgata atcctagcct agtgctactc    480
ttcaatagtt gctcctgatg ggcactttg gtcacattgc cttggttyct cctacctcgt    540
tctcttccgc atcaagcctc tatgcccgac gacaacacct cattggcccg gaccactttg    600
agcgcgcacg caccttcgcg ccgaaggagt tgataacacc cttcaccctt gcccaatgat    660
ggagttttgg tctatttgtc atgatcacct cacattcact agatcacgga tcctggaaga    720
gggtgtggaa gccagaccag cttgtccctg ttcttgcaga ctcaggtcag ctcctagcgg    780
ctatcacagc tcaggattat caagtcccgt aaagtccaga ccctttcat tgtatgatgc    840
tgcctaattt gcgctatctc tatgccgtag cagccgtctt ggctacaact ggctgccatg    900
gctgaagcat cgtgagatct ataaaggtct ccgaatcctc ggtgaagtca gaatcgtctc    960
tccacaccag tcaacaacaa gcttctttct cttacagctt agcctgagca cattcacaga   1020
actcttccct tcttttcgtc aatatgctgt tcaagtcatg gcaactggca gcagcctccg   1080
ggctcctgtc tggagtcctc ggcatcccga tggacaccgg cagccacccc attgaggctg   1140
ttgatcccga agtgaagact gaggtcttcg ctgactccct ccttgctgca gcaggcgatg   1200
acgactggga gtcacctcca tacaacttgc tttacaggtg agacacctgt cccacctgtt   1260
ttccctcgat aactaactct tataggaatg ccctgccaat tccacctgtc aagcagccca   1320
agatgtatgt ctttgatttt ctacgaagca actcggcccc gactaatgta ttctaggatc   1380
attaccaacc ctgtcaccgg caaggacatt tggtactatg agatcgagat caagccattt   1440
cagcaaaggg tgagtttgct cagaaacctt gtggtaatta atcattgtta ctgacccttt   1500
cagatttacc ccaccttgcg ccctgccact ctcgtcggct acgatggcat gagccctggt   1560
cctactttca atgttcccag aggaacagag actgtagtta ggttcatcaa caatgccacc   1620
gtggagaact cggtccatct gcacggctcc ccatcgcgtg cccctttcga tggttgggct   1680
gaagatgtga ccttccctgg cgagtacaag gattactact ttcccaacta ccaatccgcc   1740
cgccttctgt ggtaccatga ccacgctttc atgaaggtat gctacgagcc tttatctttc   1800
ttggctacct ttggctaacc aacttccttt cgtagactgc tgagaatgcc tactttggtc   1860
aggctggcgc ctacattatc aacgacgagg ctgaggatgc tctcggtctt cctagtggct   1920
atggcgagtt cgatatccct ctgatcctga cggccaagta ctataacgcc gatggtaccc   1980
tgcgttcgac cgagggtgag gaccaggacc tgtggggaga tgtcatccat gtcaacggac   2040
```

-continued

```
agccatggcc tttccttaac gtccagcccc gcaagtaccg tttccgattc ctcaacgctg   2100
ccgtgtctcg tgcttggctc ctctacctcg tcaggaccag ctctcccaac gtcagaattc   2160
ctttccaagt cattgcctct gatgctggtc tccttcaagc cccgttcag acctctaacc   2220
tctaccttgc tgttgccgag cgttacgaga tcattattgg tatgccctcc cctctcacga   2280
atgagtcaag aactctaaga ctaacacttg tagacttcac caactttgct ggccagactc   2340
ttgacctgcg caacgttgct gagaccaacg atgtcggcga cgaggatgag tacgctcgca   2400
ctctcgaggt gatgcgcttc gtcgtcagct ctggcactgt tgaggacaac agccaggtcc   2460
cctccactct ccgtgacgtt cctttccctc ctcacaagga aggccccgcc gacaagcact   2520
tcaagtttga acgcagcaac ggacactacc tgatcaacga tgttggcttt gccgatgtca   2580
atgagcgtgt cctggccaag cccgagctcg gcaccgttga ggtctgggag ctcgagaact   2640
cctctggagg ctggagccac cccgtccaca ttcaccttgt tgacttcaag atcctcaagc   2700
gaactggtgg tcgtggccag gtcatgccct acgagtctgc tggtcttaag gatgtcgtct   2760
ggttgggcag gggtgagacc ctgaccatcg aggcccacta ccaaccctgg actggagctt   2820
acatgtggca ctgtcacaac ctcattcacg aggataacga catgatggct gtattcaacg   2880
tcaccgccat ggaggagaag ggatatcttc aggaggactt cgaggacccc atgaacccca   2940
agtggcgcgc cgttccttac aaccgcaacg acttccatgc tcgcgctgga aacttctccg   3000
ccgagtccat cactgcccga gtgcaggagc tggccgagca ggagccgtac aaccgcctcg   3060
atgagatcct ggaggatctt ggaatcgagg agtaaacccc gagccacaag ctctacaatc   3120
gttttgagtc ttaagacgag gctcttggtg cgtattcttt tcttccctac ggggaactcc   3180
gctgtccact gcgatgtgaa ggaccatcac aaagcaacgt atatattgga ctcaccactg   3240
tcattaccgc ccacttgtac ctattcgatt cttgttcaaa cttttctagt gcgagagtgt   3300
ccatagtcaa gaaacgccca tagggctatc gtctaaactg aactattgtg tggtctgtga   3360
cgtggagtag atgtcaattg tgatgagaca cagtaaatac ggtatatctt ttcctaggac   3420
tacaggatca gtttctcatg agattacatc cgtctaatgt ttgtccatga gagtctagct   3480
aaggttgaga atgcatcaga cggaatcatt tgatgctctc agctcgtatt accgatgtaa   3540
gacaagttag gtaagttgct tggtatccga aaatgactca ggctccctca ttaggttgca   3600
tgtgaaaacc ttcagcaact catgggtgtt gggaccaaat catccatacc tgattttgat   3660
aactgacctg ggtcaat                                                  3677
```

```

<210> SEQ ID NO 2
<211> LENGTH: 594
<212> TYPE: PRT
<213> ORGANISM: Stachybotrys chartarum

<400> SEQUENCE: 2

Met Leu Phe Lys Ser Trp Gln Leu Ala Ala Ala Ser Gly Leu Leu Ser
 1               5                  10                  15

Gly Val Leu Gly Ile Pro Met Asp Thr Gly Ser His Pro Ile Glu Ala
            20                  25                  30

Val Asp Pro Glu Val Lys Thr Glu Val Phe Ala Asp Ser Leu Leu Ala
        35                  40                  45

Ala Ala Gly Asp Asp Asp Trp Glu Ser Pro Pro Tyr Asn Leu Leu Tyr
    50                  55                  60

Arg Asn Ala Leu Pro Ile Pro Pro Val Lys Gln Pro Lys Met Ile Ile
65                  70                  75                  80
```

-continued

```
Thr Asn Pro Val Thr Gly Lys Asp Ile Trp Tyr Glu Ile Glu Ile
                85                  90                  95
Lys Pro Phe Gln Gln Arg Ile Tyr Pro Thr Leu Arg Pro Ala Thr Leu
            100                 105                 110
Val Gly Tyr Asp Gly Met Ser Pro Gly Pro Thr Phe Asn Val Pro Arg
        115                 120                 125
Gly Thr Glu Thr Val Val Arg Phe Ile Asn Asn Ala Thr Val Glu Asn
    130                 135                 140
Ser Val His Leu His Gly Ser Pro Ser Arg Ala Pro Phe Asp Gly Trp
145                 150                 155                 160
Ala Glu Asp Val Thr Phe Pro Gly Glu Tyr Lys Asp Tyr Tyr Phe Pro
                165                 170                 175
Asn Tyr Gln Ser Ala Arg Leu Leu Trp Tyr His Asp His Ala Phe Met
            180                 185                 190
Lys Thr Ala Glu Asn Ala Tyr Phe Gly Gln Ala Gly Ala Tyr Ile Ile
        195                 200                 205
Asn Asp Glu Ala Glu Asp Ala Leu Gly Leu Pro Ser Gly Tyr Gly Glu
    210                 215                 220
Phe Asp Ile Pro Leu Ile Leu Thr Ala Lys Tyr Tyr Asn Ala Asp Gly
225                 230                 235                 240
Thr Leu Arg Ser Thr Glu Gly Glu Asp Gln Asp Leu Trp Gly Asp Val
                245                 250                 255
Ile His Val Asn Gly Gln Pro Trp Pro Phe Leu Asn Val Gln Pro Arg
            260                 265                 270
Lys Tyr Arg Phe Arg Phe Leu Asn Ala Ala Val Ser Arg Ala Trp Leu
        275                 280                 285
Leu Tyr Leu Val Arg Thr Ser Ser Pro Asn Val Arg Ile Pro Phe Gln
    290                 295                 300
Val Ile Ala Ser Asp Ala Gly Leu Leu Gln Ala Pro Val Gln Thr Ser
305                 310                 315                 320
Asn Leu Tyr Leu Ala Val Ala Glu Arg Tyr Glu Ile Ile Ile Asp Phe
                325                 330                 335
Thr Asn Phe Ala Gly Gln Thr Leu Asp Leu Arg Asn Val Ala Glu Thr
            340                 345                 350
Asn Asp Val Gly Asp Glu Asp Glu Tyr Ala Arg Thr Leu Glu Val Met
        355                 360                 365
Arg Phe Val Val Ser Ser Gly Thr Val Glu Asp Asn Ser Gln Val Pro
    370                 375                 380
Ser Thr Leu Arg Asp Val Pro Phe Pro Pro His Lys Glu Gly Pro Ala
385                 390                 395                 400
Asp Lys His Phe Lys Phe Glu Arg Ser Asn Gly His Tyr Leu Ile Asn
                405                 410                 415
Asp Val Gly Phe Ala Asp Val Asn Glu Arg Val Leu Ala Lys Pro Glu
            420                 425                 430
Leu Gly Thr Val Glu Val Trp Glu Leu Glu Asn Ser Ser Gly Gly Trp
        435                 440                 445
Ser His Pro Val His Ile His Leu Val Asp Phe Lys Ile Leu Lys Arg
    450                 455                 460
Thr Gly Gly Arg Gly Gln Val Met Pro Tyr Glu Ser Ala Gly Leu Lys
465                 470                 475                 480
Asp Val Val Trp Leu Gly Arg Gly Glu Thr Leu Thr Ile Glu Ala His
                485                 490                 495
```

-continued

```
Tyr Gln Pro Trp Thr Gly Ala Tyr Met Trp His Cys His Asn Leu Ile
            500                 505                 510

His Glu Asp Asn Asp Met Met Ala Val Phe Asn Val Thr Ala Met Glu
            515                 520                 525

Glu Lys Gly Tyr Leu Gln Glu Asp Phe Glu Asp Pro Met Asn Pro Lys
        530                 535                 540

Trp Arg Ala Val Pro Tyr Asn Arg Asn Asp Phe His Ala Arg Ala Gly
545                 550                 555                 560

Asn Phe Ser Ala Glu Ser Ile Thr Ala Arg Val Gln Glu Leu Ala Glu
                565                 570                 575

Gln Glu Pro Tyr Asn Arg Leu Asp Glu Ile Leu Glu Asp Leu Gly Ile
            580                 585                 590

Glu Glu
```

<210> SEQ ID NO 3
<211> LENGTH: 2905
<212> TYPE: DNA
<213> ORGANISM: Bipolaris spicifera

<400> SEQUENCE: 3

```
gtggcgtcgg ggatccacct gaatcatgag atataaagag agggatgttc tgtcaacaat      60
aatcccatca tcagcttttg aacattctca gctcatcaaa gattttcttc aagatggtcg     120
ccaaatacct cttctcagca cttcaactcg tttcaattgc gaaaggcata tacggygtcg     180
ctttgagcga acgtcccgcc aaatttgtcg acaacacccc cgacgaagaa aaggctgcct     240
tggcgtcaat tgttgaagat gaccctgcgg atgttgtcaa catgctgaaa gactggcaaa     300
gcccggagta tcctctcatt tttcgccaac cactgcccat ccctccagcc aaggaaccaa     360
agtagtgagt gttcaatcgc atcgacaggt ttcttagaat atactcacca tccacagtaa     420
actcacgaat cctgtcacaa acaaggagat atggtactac gagattgtca tcaaaccctt     480
cacccagcag gtctatccaa gcctgcgccc tgctcgttta gtaggctatg acggcatctc     540
cccaggtcct acgatcatag tgccgagagg aacagaagct gttgtacggt ttataaacca     600
gggtgatcgc gaaagctcca tccatctcca cggctccccc tcccgtgccc cttttgacgg     660
atgggctgat gatatgatca tgaaggggga atacaaaggt acgatagcgt gtgattctac     720
gcatcaggaa gcctctatca tactaacagg actttcttct cagactacta ctacccgaac     780
aaccaagctg ccagattttt gtggtaccac gatcatgcta tgcatgttgt aagtctttac     840
cgacttttca tggtagtgaa acggaaggat taagctaaca tctgtgcaga ccgcagaaaa     900
tgcctatttc gggcaagccg cgcgcctacct gatcacagac ccggctgagg atgctctcgg     960
ccttccttca ggttacggaa aatacgacat tccgctggtc ctcagttcca agtactacaa    1020
cgccgatgga actcttaaga ccagtgtggg agaagacaag agtgtttggg gcgacatcat    1080
ccatgtcaac ggtcagccct ggccattctt aaatgttgag cctcgaaagt atcgtcttcg    1140
attcctcaac gcggctgttt ctaggaactt tgcccttac ttcgtcaagc aagacaacac    1200
tgccactagg cttcctttcc aggtcattgc ctctgatgca gggctactca cacacccggt    1260
tcaaacctca gatatgtatg ttgcagccga agaacgctac gagattgtgt tcgatttcgc    1320
gccctatgcc ggccaaacgt tggatctgcg caacttcgca aaggcaatg gtatcggtac    1380
cgacgacgac tacgcaaaca ctgacaaggt catgcgtttc cacgtcagca gccaaacagt    1440
cgtcgataac tccgtggtac ccgagcagct atctcagatc cagttccccg cggacaaaac    1500
cgacatagac catcacttcc gtttccatcg taccaacggc gagtggcgca tcaacggcat    1560
```

```
cgggtttgca gacgtcgaga accgtgttct tgccaaggta ccgcgcggta ctgtcgagct    1620
ttgggaactt gagaacagct ccggcggctg gtcacacccc atccacgtcc acctagtaga    1680
cttccgagtc gtcgcacgct acggcgacga aggcactcgc ggcgtcatgc cctatgaggc    1740
cgccggtctc aaggacgtcg tgtggctcgg ccgtcacgag acggtcctcg tcgaagcaca    1800
ttacgcccca tgggacggag tctacatgtt ccactgccac aacctcatcc acgaagacca    1860
agacatgatg gccgccttcg acgtgactaa actccagaac tttgggtaca acgagacgac    1920
tgatttccac gatcctgagg atcctcgctg gtcagcaaga cctttcaccg cgggtgatct    1980
cacggcgcga tcgggtatct tttcagaaga atccatcagg gctagagtaa atgagttggc    2040
gctcgagcag cottacagcg aactcgcaca agttacagcc tcgctcgagc agtactacaa    2100
gacgaaccag aaacgccacg acgagtgcga agacatgcct gctggcccta tccccgtta     2160 tcgtaggttt caggtctgat tcaagttgtt ttggtggtgc aacttctcct tcttctctcc    2220
attgaactta attgtagatg atggatacac actcacttct cccttctat ctcgacgctt     2280 tggccatttt atttggtctt attgtgctat atactgtcta tttctctttc gtatacgagc    2340
aatgtatgtc ttggtcggag tcttgtggag ctgctgaggt gacacctcgc gacgccatct    2400
tagcagtttt cgtaactctc gtctatttgt gattactttg ttccttaatc agtaacagct    2460
tgatgttaga ttagcaatga gacgaacgat gaagcaatct gagatggatc ctttttttt     2520 cctaatattt gtatactaaa gaatgtgaac aatgccgttt tatgaaatgc tcataacatg    2580
cagcatattt actttgttct atttcatttc attttcatat gtacgcatat cctcggcatc    2640
agacaagaga cgcgacaacg ctctctgcat cccttctcgg cccgtaattc cgtagaaaat    2700
gaccgacggg aaagcagtcc tccacgcgct ccatgctcat catgctgcgt actatgtatc    2760
cccttccaac gcggatggcg cggatgtcgc tgcgaaccca ttgaatgggc atcacgacag    2820
ccatcatgtc gctaaggacg gattcttctt cggatgcaat gcttgtgagg gggttttctg    2880
catcccagca agatgaggtg gatcc                                          2905
```

<210> SEQ ID NO 4
<211> LENGTH: 627
<212> TYPE: PRT
<213> ORGANISM: Bipolaris spicifera

<400> SEQUENCE: 4

```
Met Val Ala Lys Tyr Leu Phe Ser Ala Leu Gln Leu Val Ser Ile Ala
 1               5                  10                  15

Lys Gly Ile Tyr Gly Val Ala Leu Ser Glu Arg Pro Ala Lys Phe Val
            20                  25                  30

Asp Asn Thr Pro Asp Glu Glu Lys Ala Ala Leu Ala Ser Ile Val Glu
        35                  40                  45

Asp Asp Pro Ala Asp Val Val Asn Met Leu Lys Asp Trp Gln Ser Pro
    50                  55                  60

Glu Tyr Pro Leu Ile Phe Arg Gln Pro Leu Pro Ile Pro Pro Ala Lys
65                  70                  75                  80

Glu Pro Asn Lys Leu Thr Asn Pro Val Thr Asn Lys Glu Ile Trp Tyr
                85                  90                  95

Tyr Glu Ile Val Ile Lys Pro Phe Thr Gln Gln Val Tyr Pro Ser Leu
            100                 105                 110

Arg Pro Ala Arg Leu Val Gly Tyr Asp Gly Ile Ser Pro Gly Pro Thr
        115                 120                 125
```

```
Ile Ile Val Pro Arg Gly Thr Glu Ala Val Val Arg Phe Ile Asn Gln
    130                 135                 140

Gly Asp Arg Glu Ser Ser Ile His Leu His Gly Ser Pro Ser Arg Ala
145                 150                 155                 160

Pro Phe Asp Gly Trp Ala Asp Met Ile Met Lys Gly Glu Tyr Lys
                165                 170                 175

Asp Tyr Tyr Pro Asn Asn Gln Ala Ala Arg Phe Leu Trp Tyr His
        180                 185                 190

Asp His Ala Met His Val Thr Ala Glu Asn Ala Tyr Phe Gly Gln Ala
            195                 200                 205

Gly Ala Tyr Leu Ile Thr Asp Pro Ala Glu Asp Ala Leu Gly Leu Pro
210                 215                 220

Ser Gly Tyr Gly Lys Tyr Asp Ile Pro Leu Val Leu Ser Ser Lys Tyr
225                 230                 235                 240

Tyr Asn Ala Asp Gly Thr Leu Lys Thr Ser Val Gly Glu Asp Lys Ser
                245                 250                 255

Val Trp Gly Asp Ile Ile His Val Asn Gly Gln Pro Trp Pro Phe Leu
            260                 265                 270

Asn Val Glu Pro Arg Lys Tyr Arg Leu Arg Phe Leu Asn Ala Ala Val
        275                 280                 285

Ser Arg Asn Phe Ala Leu Tyr Phe Val Lys Gln Asp Asn Thr Ala Thr
    290                 295                 300

Arg Leu Pro Phe Gln Val Ile Ala Ser Asp Ala Gly Leu Leu Thr His
305                 310                 315                 320

Pro Val Gln Thr Ser Asp Met Tyr Val Ala Ala Glu Arg Tyr Glu
                325                 330                 335

Ile Val Phe Asp Phe Ala Pro Tyr Ala Gly Gln Thr Leu Asp Leu Arg
            340                 345                 350

Asn Phe Ala Lys Ala Asn Gly Ile Gly Thr Asp Asp Tyr Ala Asn
        355                 360                 365

Thr Asp Lys Val Met Arg Phe His Val Ser Ser Gln Thr Val Val Asp
    370                 375                 380

Asn Ser Val Val Pro Glu Gln Leu Ser Gln Ile Gln Phe Pro Ala Asp
385                 390                 395                 400

Lys Thr Asp Ile Asp His His Phe Arg Phe His Arg Thr Asn Gly Glu
                405                 410                 415

Trp Arg Ile Asn Gly Ile Gly Phe Ala Asp Val Glu Asn Arg Val Leu
            420                 425                 430

Ala Lys Val Pro Arg Gly Thr Val Glu Leu Trp Glu Leu Glu Asn Ser
        435                 440                 445

Ser Gly Gly Trp Ser His Pro Ile His Val His Leu Val Asp Phe Arg
    450                 455                 460

Val Val Ala Arg Tyr Gly Asp Glu Gly Thr Arg Gly Val Met Pro Tyr
465                 470                 475                 480

Glu Ala Ala Gly Leu Lys Asp Val Val Trp Leu Gly Arg His Glu Thr
                485                 490                 495

Val Leu Val Glu Ala His Tyr Ala Pro Trp Asp Gly Val Tyr Met Phe
            500                 505                 510

His Cys His Asn Leu Ile His Glu Asp Gln Asp Met Met Ala Ala Phe
        515                 520                 525

Asp Val Thr Lys Leu Gln Asn Phe Gly Tyr Asn Glu Thr Thr Asp Phe
    530                 535                 540

His Asp Pro Glu Asp Pro Arg Trp Ser Ala Arg Pro Phe Thr Ala Gly
```

-continued

```
545                 550                 555                 560
Asp Leu Thr Ala Arg Ser Gly Ile Phe Ser Glu Glu Ser Ile Arg Ala
                565                 570                 575

Arg Val Asn Glu Leu Ala Leu Glu Gln Pro Tyr Ser Glu Leu Ala Gln
                580                 585                 590

Val Thr Ala Ser Leu Glu Gln Tyr Tyr Lys Thr Asn Gln Lys Arg His
                595                 600                 605

Asp Glu Cys Glu Asp Met Pro Ala Gly Pro Ile Pro Arg Tyr Arg Arg
    610                 615                 620

Phe Gln Val
625
```

<210> SEQ ID NO 5
<211> LENGTH: 1791
<212> TYPE: DNA
<213> ORGANISM: Artificial Sequence
<220> FEATURE:
<223> OTHER INFORMATION: cDNA

<400> SEQUENCE: 5

```
gtcaatatgc tgttcaagtc atggcaactg gcagcagcct ccgggctcct gtctggagtc      60
ctcggcatcc cgatggacac cggcagccac cccattgagg ctgttgatcc cgaagtgaag     120
actgaggtct cgctgactc cctccttgct gcagcaggcg atgacgactg ggagtcacct     180
ccatacaact tgctttacag gaatgccctg ccaattccac ctgtcaagca gcccaagatg     240
atcattacca accctgtcac cggcaaggac atttggtact atgagatcga gatcaagcca     300
tttcagcaaa ggatttaccc caccttgcgc cctgccactc tcgtcggcta cgatggcatg     360
agccctggtc ctactttcaa tgttcccaga ggaacagaga ctgtagttag gttcatcaac     420
aatgccaccg tggagaactc ggtccatctg cacggctccc catcgcgtgc ccctttcgat     480
ggttgggctg aagatgtgac cttccctggc gagtacaagg attactactt tcccaactac     540
caatccgccc gccttctgtg gtaccatgac cacgctttca tgaagactgc tgagaatgcc     600
tactttggtc aggctggcgc ctacattatc aacgacgagg ctgaggatgc tctcggtctt     660
cctagtggct atggcgagtt cgatatccct ctgatcctga cggccaagta ctataacgcc     720
gatggtaccc tgcgttcgac cgagggtgag gaccaggacc tgtggggaga tgtcatccat     780
gtcaacggac agccatggcc tttccttaac gtccagcccc gcaagtaccg tttccgattc     840
ctcaacgctg ccgtgtctcg tgcttggctc tctacctcg tcaggaccag ctctcccaac     900
gtcagaattc ctttccaagt cattgcctct gatgctggtc tccttcaagc ccccgttcag     960
acctctaacc tctaccttgc tgttgccgag cgttacgaga tcattattga cttcaccaac    1020
tttgctggcc agactcttga cctgcgcaac gttgctgaga ccaacgatgt cggcgacgag    1080
gatgagtacg ctcgcactct cgaggtgatg cgcttcgtcg tcagctctgg cactgttgag    1140
gacaacagcc aggtcccctc cactctccgt gacgttcctt ccctcctca aaggaaggc    1200
cccgccgaca gcacttcaa gtttgaacgc agcaacggac actacctgat caacgatgtt    1260
ggctttgccg atgtcaatga gcgtgtcctg gccaagcccg agctcggcac cgttgaggtc    1320
tgggagctcg agaactcctc tggaggctgg agccaccccg tccacattca ccttgttgac    1380
ttcaagatcc tcaagcgaac tggtggtcgt ggccaggtca tgcctacga gtctgctggt    1440
cttaaggatg tcgtctggtt gggcagggt gagaccctga ccatcgaggc ccactaccaa    1500
ccctggactg gagcttacat gtggcactgt cacaacctca ttcacgagga taacgacatg    1560
```

```
atggctgtat tcaacgtcac cgccatggag gagaagggat atcttcagga ggacttcgag   1620
gaccccatga accccaagtg gcgcgccgtt ccttacaacc gcaacgactt ccatgctcgc   1680
gctggaaact tctccgccga gtccatcact gcccgagtgc aggagctggc cgagcaggag   1740
ccgtacaacc gcctcgatga gatcctggag gatcttggaa tcgaggagta a            1791
```

<210> SEQ ID NO 6
<211> LENGTH: 2063
<212> TYPE: DNA
<213> ORGANISM: Curvularia pallescens

<400> SEQUENCE: 6

```
atggttgcca aatacctctt ctcggcactt caactcgctt caattgcgaa aggcatatac     60
ggcgttgctt tgagcgagcg tcctgccaaa tatattgacg aaaccccga cgaagaaaag    120 gctgccctgg cagccatcgt tgaagatgac cctgccgatg ttttcagaat cctgaaggac    180
tggcaaagcc cggagtatcc catccttttt cgcgaggcac tgcccatccc tccagccaag    240
gaaccgaagt agtgagtctt gaattgcatg acaggtttc ctagaatatg ctcacccatc     300
cgcagtaaaa tgacgaatcc tgtcacaaac aaggagatct ggtactacga gattgtcatc    360 aaaccctta accaacaggt ctatccaagt ctacgtcctg ctcgcttggt aggctatgat     420
ggcatttcac caggccctac gatcatcgtg ccgagaggaa cagaagccgt tgtacgattc    480
gtaaaccagg gtgatcgcga gagttcgatt catcttcatg gttctccctc ccgtgccccc    540
tttgacggat gggctgaaga tttgattatg aagggccaat tcaaaggtac aacagaacaa    600
tcttatgcat cagggtgcct cttttatact aacacgactc gttcttagac tactactacc    660
cgaacaacca ggctgccaga ttcctgtggt accacgatca tgctatgcat gttgtaagtc    720
ttgcagacta atcatgggag cgaaacggaa agatcgggct gacacttatg cagactgcgg    780
aaaatgccta ttttggacag gctggcgcct acctgatcac agacccagct gaggacgccc    840
tcggccttcc ttcgggttac ggaaaatacg acatcccact ggtgctcagt tccaagttct    900
acaacagtga tggaactctc cagaccagtg tgggagaaga caacagtctc tggggcgacg    960
tcatccatgt caacggtcag ccctggccat tcttcaacgt tgagcctcga agtatcgcc   1020 ttcgattcct caatgcggct gtttctcgga acttttgccct ctatttcgtc aagcaacaag   1080
ccactgctac tagacttcct ttccaggtca ttgcctctga tgcagggcta ctcacgcacc   1140
cggtccaaac ctcagatatt tacgtggcag cagcagagcg ctacgagatt gtattcgact   1200
ttgcgcctta tgcaggccag acgatagatt tgcgtaactt tgcaaaggcc aatggggtcg   1260
gcaccgatga cgattatgca aacactgaca aggtcatgcg cttccatgtc agcagccaag   1320
cagtcgtcga taactcggtg gtacccgcac agctatctca gatccagttc cccgccgaca   1380
aaaccggcat cgaccaccac ttccgcttcc atcgcaccaa cagcgagtgg cgcatcaacg   1440
gcatcgggtt tgcagacgtc cagaaccgta tcctggccaa ggtaccgcgc ggcactgtcg   1500
agctatggga actcgagaac agctccggcg gctggtcgca ccccatccac gtccacctgg   1560
tcgacttccg agtcgtcgca cgctacggtg acgaaagcac tcgcggcgtc atgccctacg   1620
agtccgccgg tctcaaggac gtcgtgtggc tcggccgcca cgagacggtg ctcgtcgaag   1680
cacactacgc ccctgggac ggagtctaca tgttccactg ccacaacctg atccacgaag   1740
accaagacat gatggccgcg tttgacgtga ctaagctcca gaactttggc tacaacgaga   1800
cgacggattt ccacgacccg gaagattctc gctggtctgc aagacccttc accgcggctg   1860
acttgacggc gcgatcgggt atcttctcag aagcatccat cagggctaga gtgaacgagt   1920
```

```
tggcgctgga acagccgtac agcgaactgg cacaggtcac ggcctcgctc gagcagtact   1980
acaagacgaa caagaaacgc caggccgagt gcgaagacat gcctgctggc cccattcccc   2040
gttatcgcag gtttcaggtc tga                                           2063
```

<210> SEQ ID NO 7
<211> LENGTH: 627
<212> TYPE: PRT
<213> ORGANISM: Curvularia pallescens

<400> SEQUENCE: 7

```
Met Val Ala Lys Tyr Leu Phe Ser Ala Leu Gln Leu Ala Ser Ile Ala
 1               5                  10                  15

Lys Gly Ile Tyr Gly Val Ala Leu Ser Glu Arg Pro Ala Lys Tyr Ile
            20                  25                  30

Asp Glu Thr Pro Asp Glu Lys Ala Ala Leu Ala Ala Ile Val Glu
        35                  40                  45

Asp Asp Pro Ala Asp Val Phe Arg Ile Leu Lys Asp Trp Gln Ser Pro
    50                  55                  60

Glu Tyr Pro Ile Leu Phe Arg Glu Ala Leu Pro Ile Pro Pro Ala Lys
65                  70                  75                  80

Glu Pro Asn Lys Met Thr Asn Pro Val Thr Asn Lys Glu Ile Trp Tyr
                85                  90                  95

Tyr Glu Ile Val Ile Lys Pro Phe Asn Gln Gln Val Tyr Pro Ser Leu
            100                 105                 110

Arg Pro Ala Arg Leu Val Gly Tyr Asp Gly Ile Ser Pro Gly Pro Thr
        115                 120                 125

Ile Ile Val Pro Arg Gly Thr Glu Ala Val Val Arg Phe Val Asn Gln
    130                 135                 140

Gly Asp Arg Glu Ser Ser Ile His Leu His Gly Ser Pro Ser Arg Ala
145                 150                 155                 160

Pro Phe Asp Gly Trp Ala Glu Asp Leu Ile Met Lys Gly Gln Phe Lys
                165                 170                 175

Asp Tyr Tyr Tyr Pro Asn Asn Gln Ala Ala Arg Phe Leu Trp Tyr His
            180                 185                 190

Asp His Ala Met His Val Thr Ala Glu Asn Ala Tyr Phe Gly Gln Ala
        195                 200                 205

Gly Ala Tyr Leu Ile Thr Asp Pro Ala Glu Asp Ala Leu Gly Leu Pro
    210                 215                 220

Ser Gly Tyr Gly Lys Tyr Asp Ile Pro Leu Val Leu Ser Ser Lys Phe
225                 230                 235                 240

Tyr Asn Ser Asp Gly Thr Leu Gln Thr Ser Val Gly Glu Asp Asn Ser
                245                 250                 255

Leu Trp Gly Asp Val Ile His Val Asn Gly Gln Pro Trp Pro Phe Phe
            260                 265                 270

Asn Val Glu Pro Arg Lys Tyr Arg Leu Arg Phe Leu Asn Ala Ala Val
        275                 280                 285

Ser Arg Asn Phe Ala Leu Tyr Phe Val Lys Gln Gln Ala Thr Ala Thr
    290                 295                 300

Arg Leu Pro Phe Gln Val Ile Ala Ser Asp Ala Gly Leu Leu Thr His
305                 310                 315                 320

Pro Val Gln Thr Ser Asp Ile Tyr Val Ala Ala Glu Arg Tyr Glu
                325                 330                 335

Ile Val Phe Asp Phe Ala Pro Tyr Ala Gly Gln Thr Ile Asp Leu Arg
```

```
                         340                     345                     350
Asn Phe Ala Lys Ala Asn Gly Val Gly Thr Asp Asp Tyr Ala Asn
                355                     360                     365
Thr Asp Lys Val Met Arg Phe His Val Ser Ser Gln Ala Val Val Asp
        370                     375                     380
Asn Ser Val Val Pro Ala Gln Leu Ser Gln Ile Gln Phe Pro Ala Asp
385                     390                     395                     400
Lys Thr Gly Ile Asp His His Phe Arg Phe His Arg Thr Asn Ser Glu
                405                     410                     415
Trp Arg Ile Asn Gly Ile Gly Phe Ala Asp Val Gln Asn Arg Ile Leu
                420                     425                     430
Ala Lys Val Pro Arg Gly Thr Val Glu Leu Trp Glu Leu Glu Asn Ser
                435                     440                     445
Ser Gly Gly Trp Ser His Pro Ile His Val His Leu Val Asp Phe Arg
        450                     455                     460
Val Val Ala Arg Tyr Gly Asp Glu Ser Thr Arg Gly Val Met Pro Tyr
465                     470                     475                     480
Glu Ser Ala Gly Leu Lys Asp Val Val Trp Leu Gly Arg His Glu Thr
                485                     490                     495
Val Leu Val Glu Ala His Tyr Ala Pro Trp Asp Gly Val Tyr Met Phe
                500                     505                     510
His Cys His Asn Leu Ile His Glu Asp Gln Asp Met Met Ala Ala Phe
                515                     520                     525
Asp Val Thr Lys Leu Gln Asn Phe Gly Tyr Asn Glu Thr Thr Asp Phe
        530                     535                     540
His Asp Pro Glu Asp Ser Arg Trp Ser Ala Arg Pro Phe Thr Ala Ala
545                     550                     555                     560
Asp Leu Thr Ala Arg Ser Gly Ile Phe Ser Glu Ala Ser Ile Arg Ala
                565                     570                     575
Arg Val Asn Glu Leu Ala Leu Glu Gln Pro Tyr Ser Glu Leu Ala Gln
                580                     585                     590
Val Thr Ala Ser Leu Glu Gln Tyr Tyr Lys Thr Asn Lys Lys Arg Gln
                595                     600                     605
Ala Glu Cys Glu Asp Met Pro Ala Gly Pro Ile Pro Arg Tyr Arg Arg
                610                     615                     620
Phe Gln Val
625

<210> SEQ ID NO 8
<211> LENGTH: 858
<212> TYPE: DNA
<213> ORGANISM: Amerosporium atrum
<220> FEATURE:
<221> NAME/KEY: misc_feature
<222> LOCATION: (1)...(858)
<223> OTHER INFORMATION: n = A,T,C or G

<400> SEQUENCE: 8
caccgccgag aacgcttact ttggtcaagc tggcttttac attctgcacg accccgctga      60
agatgcattg ggtctgcctt ctggcaagta tgatgtacct cttgcactgt cctccaagca     120
gtacaacagc gacggtaccc tcttcgaccc caaggacgag accgattcac tgttcggcga     180
tgtcatccac gtcaacggac agccatggcc ctactttaag gtcgagcctc gcaagtaccg     240
tctccgcttc ctcaatgctg ctatcagccg tgccttcaag ctcactttcg aggctgatgg     300
caaagtgatc aactttcctg tcatcggtgc cgatactggt ctcttgacca agcctgttca     360
```

-continued

```
gacaagcaac cttgagatct ctatggccga gcgctgggag gttgtttttg acttcagcca    420
attttccggg aagaacgtca ccctcaagaa cggtcgcgat gtgcagcacg atgaggacta    480
caactccacc gacaaagtca tgcagttcgt tgttggcaag gatgttacga gccaggctgg    540
taatggcaac cttcccggct ctctgcgcac tgttcccttc cctcctaaga aggggcggag    600
tcgacaggag cttcaagttc ggcagggacc ggtggccagt ggactgttaa tggcttgacc    660
ttcgctgatg tcaacaaccg catcctggct aagcccccaa cgtggtgcca tcgaggtttt    720
gggagctttg agaacttcca gcggnggntg gtcttaccct tgtccacatc cacctgggtc    780
gactttccag atncttgtct tgcactggan gcaaggcncc ccgttntaac tncnanaaag    840
gaagcacttt caagggcg                                                  858
```
<210> SEQ ID NO 9
<211> LENGTH: 114
<212> TYPE: PRT
<213> ORGANISM: Amerosporium atrum
<220> FEATURE:
<221> NAME/KEY: VARIANT
<222> LOCATION: (1)...(114)
<223> OTHER INFORMATION: Xaa = space of unknown number of aa

<400> SEQUENCE: 9

```
Thr Ala Glu Asn Ala Tyr Phe Gly Gln Ala Gly Phe Tyr Ile Leu His
 1               5                  10                  15

Asp Pro Ala Glu Asp Ala Leu Gly Leu Pro Ser Gly Lys Tyr Asp Val
            20                  25                  30

Pro Leu Ala Leu Ser Leu Lys Ala Tyr Asn Ser Asp Gly Thr Leu Phe
        35                  40                  45

Asp Pro Lys Asp Glu Thr Asp Ser Leu Phe Gly Asp Val Ile His Val
    50                  55                  60

Asn Gly Gln Pro Trp Pro Tyr Leu Lys Val Glu Pro Arg Lys Tyr Arg
65                  70                  75                  80

Leu Arg Phe Leu Asn Ala Ala Ile Ser Arg Ala Phe Lys Xaa Val Trp
                85                  90                  95

Glu Leu Glu Asn Thr Ser Ser Gly Gly Trp Ser Tyr Pro Val His Ile
            100                 105                 110

His Leu
```

<210> SEQ ID NO 10
<211> LENGTH: 19
<212> TYPE: PRT
<213> ORGANISM: Stachybotrys chartarum
<220> FEATURE:
<221> NAME/KEY: VARIANT
<222> LOCATION: (1)...(19)
<223> OTHER INFORMATION: Xaa = Any Amino Acid

<400> SEQUENCE: 10

```
Asp Tyr Tyr Phe Pro Asn Tyr Gln Ser Ala Arg Leu Leu Xaa Tyr His
 1               5                  10                  15

Asp His Ala
```

<210> SEQ ID NO 11
<211> LENGTH: 13
<212> TYPE: PRT
<213> ORGANISM: Stachybotrys chartarum

<400> SEQUENCE: 11

Arg Gly Gln Val Met Pro Tyr Glu Ser Ala Gly Leu Lys
 1               5                  10

<210> SEQ ID NO 12
<211> LENGTH: 20
<212> TYPE: DNA
<213> ORGANISM: Artificial Sequence
<220> FEATURE:
<223> OTHER INFORMATION: degenerated primer
<221> NAME/KEY: misc_feature
<222> LOCATION: (12)...(12)
<223> OTHER INFORMATION: n = A,T,C or G
<221> NAME/KEY: misc_feature
<222> LOCATION: (15)...(20)
<223> OTHER INFORMATION: n = T or C

<400> SEQUENCE: 12
tattactttc cnaantanca                                              20

<210> SEQ ID NO 13
<211> LENGTH: 20
<212> TYPE: DNA
<213> ORGANISM: Artificial Sequence
<220> FEATURE:
<223> OTHER INFORMATION: degenerated primer
<221> NAME/KEY: misc_feature
<222> LOCATION: (1)...(20)
<223> OTHER INFORMATION: n = A,T,C or G

<400> SEQUENCE: 13
tcgtatggca tnacctgncc                                              20

<210> SEQ ID NO 14
<211> LENGTH: 18
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(20)
<223> OTHER INFORMATION: n = T or C

<400> SEQUENCE: 14
tggtaccang ancangct                                                18

<210> SEQ ID NO 15
<211> LENGTH: 18
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(1)
<223> OTHER INFORMATION: n = A or G
<221> NAME/KEY: misc_feature
<222> LOCATION: (10)...(10)
<223> OTHER INFORMATION: n = T or G

<400> SEQUENCE: 15
ngactcgtan ggcatgac                                                18

<210> SEQ ID NO 16
<211> LENGTH: 21
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (1)...(21)
<223> OTHER INFORMATION: n = A or G -continued

```
<400> SEQUENCE: 16
tcgtggatga nnttgtgnca n                                              21

<210> SEQ ID NO 17
<211> LENGTH: 21
<212> TYPE: DNA
<213> ORGANISM: Artificial Sequence
<220> FEATURE:
<223> OTHER INFORMATION: oligonucleotide primer
<221> NAME/KEY: misc_feature
<222> LOCATION: (2)...(2)
<223> OTHER INFORMATION: n = A,T,C or G
<221> NAME/KEY: misc_feature
<222> LOCATION: (5)...(10)
<223> OTHER INFORMATION: n = A or G
<221> NAME/KEY: misc_feature
<222> LOCATION: (13)...(13)
<223> OTHER INFORMATION: n = T or C
<221> NAME/KEY: misc_feature
<222> LOCATION: (15)...(15)
<223> OTHER INFORMATION: n = A or G

<400> SEQUENCE: 17
cnagacnacn tcnttnagac c                                              21
```